(12) United States Patent
Imran et al.

(10) Patent No.: US 9,044,592 B2
(45) Date of Patent: Jun. 2, 2015

(54) SUTURELESS LEAD RETENTION FEATURES

(75) Inventors: Mir A. Imran, Los Altos, CA (US);
Albert G. Burdulis, San Francisco, CA (US); Kamran Behzadian, Sunnyvale, CA (US); Fred I. Linker, Los Altos, CA (US); Nicholas C. Debeer, Montara, CA (US); Arturo Rosqueta, San Jose, CA (US)

(73) Assignee: Spinal Modulation, Inc., Menlo Park, CA (US)

( * ) Notice: Subject to any disclaimer, the term of this patent is extended or adjusted under 35 U.S.C. 154(b) by 0 days.

(21) Appl. No.: 12/022,135

(22) Filed: Jan. 29, 2008

(65) Prior Publication Data
US 2008/0183257 A1    Jul. 31, 2008

Related U.S. Application Data

(60) Provisional application No. 60/898,342, filed on Jan. 29, 2007, provisional application No. 60/998,722, filed on Oct. 12, 2007.

(51) Int. Cl.
*A61N 1/05*    (2006.01)

(52) U.S. Cl.
CPC .............. *A61N 1/0558* (2013.01); *A61N 1/057* (2013.01); *A61N 2001/0585* (2013.01)

(58) Field of Classification Search
CPC ..... A61N 1/05; A61N 1/0551; A61N 1/0553; A61N 1/0558
USPC ............... 607/126, 115–117; 606/129
See application file for complete search history.

(56) References Cited

U.S. PATENT DOCUMENTS

| | | | |
|---|---|---|---|
| 525,891 | A | 9/1894 | Fricke |
| 3,724,467 | A | 4/1973 | Avery et al. |

(Continued)

FOREIGN PATENT DOCUMENTS

| | | |
|---|---|---|
| CN | 2401143 Y | 10/2000 |
| CN | 101594907 A | 12/2009 |

(Continued)

OTHER PUBLICATIONS

Clark, Robert K. "Anatomy and physiology: understanding the human body"; Jones & Bartlett Publishers; Sudbury, MA; ISBN 0-7637-4816-6; Chapter 12; pp. 213-215; Feb. 28, 2005.

(Continued)

*Primary Examiner* — Paula J Stice
(74) *Attorney, Agent, or Firm* — Shay Glenn LLP

(57) ABSTRACT

A system includes a lead having a lead body and at least one electrode; and a retention feature disposed along the lead body proximal to the at least one electrode and configured to assist in atraumatically anchoring the lead to nearby tissue when the lead is positioned in the body. A system includes a lead having a lead body and at least one electrode; and a coiled retention feature disposed along the lead body proximal to the at least one electrode and configured to assist in anchoring the lead to nearby tissue when the lead is positioned in a body. A lead for stimulating a target neural tissue includes an elongate body; at least one electrode disposed along the elongate body; and a passive retention feature disposed along the lead body proximal to the at least one electrode and configured to assist in anchoring the elongate body to tissue near the target neural tissue.

19 Claims, 18 Drawing Sheets

(56) References Cited

U.S. PATENT DOCUMENTS

| | | | |
|---|---|---|---|
| 3,845,770 A | 11/1974 | Theeuwes et al. |
| 3,916,899 A | 11/1975 | Theeuwes et al. |
| 4,141,367 A | 2/1979 | Ferreira |
| 4,232,679 A | 11/1980 | Schulman |
| 4,298,003 A | 11/1981 | Theeuwes et al. |
| 4,313,448 A | 2/1982 | Stokes |
| 4,374,527 A | 2/1983 | Iversen |
| 4,479,491 A | 10/1984 | Martin |
| 4,549,556 A | 10/1985 | Tarjan et al. |
| 4,573,481 A | 3/1986 | Bullara |
| 4,577,642 A | 3/1986 | Stokes |
| 4,590,946 A | 5/1986 | Loeb |
| 4,607,639 A | 8/1986 | Tanagho et al. |
| 4,739,764 A | 4/1988 | Lue et al. |
| 4,786,155 A | 11/1988 | Fantone et al. |
| 4,803,988 A | 2/1989 | Thomson |
| 4,920,979 A | 5/1990 | Bullara |
| 4,940,065 A | 7/1990 | Tanagho et al. |
| 4,950,270 A | 8/1990 | Bowman et al. |
| 4,976,711 A | 12/1990 | Parins et al. |
| 5,135,525 A | 8/1992 | Biscoping et al. |
| 5,270,099 A | 12/1993 | Kamiyama et al. |
| 5,299,569 A | 4/1994 | Wernicke et al. |
| 5,344,438 A | 9/1994 | Testerman et al. |
| 5,358,514 A | 10/1994 | Schulman et al. |
| 5,370,644 A | 12/1994 | Langberg |
| 5,411,537 A | 5/1995 | Munshi et al. |
| 5,411,540 A | 5/1995 | Edell et al. |
| 5,417,719 A | 5/1995 | Hull et al. |
| 5,419,763 A | 5/1995 | Hildebrand |
| 5,458,626 A | 10/1995 | Krause |
| 5,489,294 A | 2/1996 | McVenes et al. |
| 5,505,201 A | 4/1996 | Grill et al. |
| 5,514,175 A | 5/1996 | Kim et al. |
| 5,584,835 A | 12/1996 | Greenfield |
| 5,634,462 A | 6/1997 | Tyler et al. |
| 5,643,330 A | 7/1997 | Holsheimer et al. |
| 5,702,429 A | 12/1997 | King |
| 5,711,316 A | 1/1998 | Elsberry et al. |
| 5,713,922 A | 2/1998 | King |
| 5,733,322 A * | 3/1998 | Starkebaum | 607/117 |
| 5,741,319 A | 4/1998 | Woloszko et al. |
| 5,755,750 A | 5/1998 | Petruska et al. |
| 5,776,170 A | 7/1998 | MacDonald et al. |
| 5,807,339 A | 9/1998 | Bostrom et al. |
| 5,824,021 A | 10/1998 | Rise |
| 5,865,843 A * | 2/1999 | Baudino | 607/116 |
| 5,871,531 A | 2/1999 | Struble |
| 5,885,290 A | 3/1999 | Guerrero et al. |
| 5,938,690 A | 8/1999 | Law et al. |
| 5,948,007 A | 9/1999 | Starkebaum et al. |
| 5,957,965 A * | 9/1999 | Moumane et al. | 607/117 |
| 5,983,141 A | 11/1999 | Sluijter et al. |
| 5,984,896 A * | 11/1999 | Boyd | 604/175 |
| 6,002,964 A | 12/1999 | Feler et al. |
| 6,044,297 A | 3/2000 | Sheldon et al. |
| 6,045,532 A | 4/2000 | Eggers et al. |
| 6,051,017 A | 4/2000 | Loeb et al. |
| 6,104,957 A | 8/2000 | Alo et al. |
| 6,120,467 A | 9/2000 | Schallhorn |
| 6,161,048 A | 12/2000 | Sluijter et al. |
| 6,175,764 B1 | 1/2001 | Loeb et al. |
| 6,181,965 B1 | 1/2001 | Loeb et al. |
| 6,185,455 B1 | 2/2001 | Loeb et al. |
| 6,205,359 B1 | 3/2001 | Boveja |
| 6,208,902 B1 | 3/2001 | Boveja |
| 6,214,016 B1 | 4/2001 | Williams et al. |
| 6,259,952 B1 | 7/2001 | Sluijter et al. |
| 6,298,256 B1 | 10/2001 | Meyer |
| 6,314,325 B1 | 11/2001 | Fitz |
| 6,319,241 B1 | 11/2001 | King et al. |
| 6,349,233 B1 | 2/2002 | Adams |
| 6,353,762 B1 | 3/2002 | Baudino et al. |
| 6,356,786 B1 | 3/2002 | Rezai et al. |
| 6,360,750 B1 | 3/2002 | Gerber et al. |
| 6,366,814 B1 | 4/2002 | Boveja et al. |
| 6,393,325 B1 | 5/2002 | Mann et al. |
| 6,413,255 B1 | 7/2002 | Stern |
| 6,425,887 B1 | 7/2002 | McGuckin et al. |
| 6,438,423 B1 | 8/2002 | Rezai et al. |
| 6,440,090 B1 | 8/2002 | Schallhorn |
| 6,466,821 B1 | 10/2002 | Pianca et al. |
| 6,493,588 B1 | 12/2002 | Malaney et al. |
| 6,510,347 B2 | 1/2003 | Borkan |
| 6,512,958 B1 | 1/2003 | Swoyer et al. |
| 6,516,227 B1 | 2/2003 | Meadows et al. |
| 6,517,542 B1 | 2/2003 | Papay et al. |
| 6,522,926 B1 | 2/2003 | Kieval et al. |
| 6,535,767 B1 | 3/2003 | Kronberg |
| 6,582,441 B1 | 6/2003 | He et al. |
| 6,587,725 B1 | 7/2003 | Durand et al. |
| 6,605,094 B1 | 8/2003 | Mann et al. |
| 6,606,521 B2 | 8/2003 | Paspa et al. |
| 6,611,715 B1 | 8/2003 | Boveja |
| 6,625,496 B1 | 9/2003 | Ollivier |
| 6,638,276 B2 | 10/2003 | Sharkey et al. |
| 6,658,302 B1 | 12/2003 | Kuzma et al. |
| 6,714,822 B2 | 3/2004 | King et al. |
| 6,748,276 B1 | 6/2004 | Daignault, Jr. et al. |
| 6,754,539 B1 | 6/2004 | Erickson et al. |
| 6,788,975 B1 | 9/2004 | Whitehurst et al. |
| 6,792,318 B2 * | 9/2004 | Chitre et al. | 607/126 |
| 6,832,115 B2 | 12/2004 | Borkan |
| 6,835,194 B2 | 12/2004 | Johnson et al. |
| 6,839,588 B1 | 1/2005 | Rudy |
| 6,849,075 B2 | 2/2005 | Bertolero et al. |
| 6,862,479 B1 | 3/2005 | Whitehurst et al. |
| 6,871,099 B1 | 3/2005 | Whitehurst et al. |
| 6,873,342 B2 | 3/2005 | Perry et al. |
| 6,889,094 B1 | 5/2005 | Kuzma et al. |
| 6,901,287 B2 | 5/2005 | Davis et al. |
| 6,902,547 B2 | 6/2005 | Aves et al. |
| 6,909,917 B2 | 6/2005 | Woods et al. |
| 6,928,320 B2 | 8/2005 | King |
| 6,971,391 B1 | 12/2005 | Wang et al. |
| 6,978,180 B2 | 12/2005 | Tadlock |
| 7,047,082 B1 | 5/2006 | Schrom et al. |
| 7,096,070 B1 | 8/2006 | Jenkins et al. |
| 7,127,287 B2 | 10/2006 | Duncan et al. |
| 7,333,857 B2 | 2/2008 | Campbell |
| 2001/0003799 A1 | 6/2001 | Boveja |
| 2001/0006967 A1 | 7/2001 | Crain et al. |
| 2002/0064841 A1 | 5/2002 | Klemic et al. |
| 2002/0077684 A1 | 6/2002 | Clemens et al. |
| 2002/0087113 A1 | 7/2002 | Hartlaub |
| 2002/0099430 A1 | 7/2002 | Verness |
| 2002/0116030 A1 | 8/2002 | Rezai |
| 2002/0128694 A1 | 9/2002 | Holsheimer |
| 2002/0147486 A1 * | 10/2002 | Soukup et al. | 607/122 |
| 2002/0198527 A1 | 12/2002 | Muckter |
| 2003/0018367 A1 | 1/2003 | Dilorenzo |
| 2003/0023241 A1 | 1/2003 | Drewry et al. |
| 2003/0045919 A1 | 3/2003 | Swoyer et al. |
| 2003/0069569 A1 | 4/2003 | Burdette et al. |
| 2003/0078633 A1 | 4/2003 | Firlik et al. |
| 2003/0088301 A1 | 5/2003 | King |
| 2003/0100933 A1 | 5/2003 | Ayal et al. |
| 2003/0114905 A1 | 6/2003 | Kuzma |
| 2003/0130577 A1 | 7/2003 | Purdy et al. |
| 2003/0144657 A1 | 7/2003 | Bowe et al. |
| 2003/0144709 A1 | 7/2003 | Zabara et al. |
| 2003/0181958 A1 | 9/2003 | Dobak, III |
| 2003/0187490 A1 | 10/2003 | Gliner |
| 2003/0195602 A1 | 10/2003 | Boling |
| 2003/0220677 A1 | 11/2003 | Doan et al. |
| 2004/0015202 A1 | 1/2004 | Chandler et al. |
| 2004/0019359 A1 | 1/2004 | Worley et al. |
| 2004/0019369 A1 | 1/2004 | Duncan et al. |
| 2004/0059404 A1 | 3/2004 | Bjorklund et al. |
| 2004/0116977 A1 | 6/2004 | Finch et al. |
| 2004/0122360 A1 | 6/2004 | Waldhauser et al. |
| 2004/0122477 A1 | 6/2004 | Whitehurst et al. |
| 2004/0122497 A1 | 6/2004 | Zhang et al. |
| 2004/0122498 A1 | 6/2004 | Zhang et al. |

(56) References Cited

U.S. PATENT DOCUMENTS

| | | |
|---|---|---|
| 2004/0147992 A1 | 7/2004 | Bluger et al. |
| 2004/0172089 A1 | 9/2004 | Whitehurst et al. |
| 2004/0210290 A1 | 10/2004 | Omar-Pasha |
| 2004/0215286 A1 | 10/2004 | Stypulkowski |
| 2004/0230273 A1 | 11/2004 | Cates et al. |
| 2004/0230280 A1* | 11/2004 | Cates et al. ............ 607/126 |
| 2004/0243210 A1 | 12/2004 | Morgan et al. |
| 2005/0027338 A1 | 2/2005 | Hill |
| 2005/0033295 A1 | 2/2005 | Wisnewski |
| 2005/0033393 A1 | 2/2005 | Daglow |
| 2005/0038489 A1 | 2/2005 | Grill |
| 2005/0070982 A1 | 3/2005 | Heruth et al. |
| 2005/0080325 A1 | 4/2005 | Erickson |
| 2005/0090885 A1 | 4/2005 | Harris et al. |
| 2005/0096718 A1* | 5/2005 | Gerber et al. ............ 607/117 |
| 2005/0149154 A1 | 7/2005 | Cohen et al. |
| 2005/0159799 A1 | 7/2005 | Daglow et al. |
| 2005/0203599 A1 | 9/2005 | Garabedian et al. |
| 2005/0222647 A1 | 10/2005 | Wahlstrand et al. |
| 2005/0251237 A1 | 11/2005 | Kuzma et al. |
| 2006/0004364 A1 | 1/2006 | Green et al. |
| 2006/0009820 A1 | 1/2006 | Royle |
| 2006/0041295 A1* | 2/2006 | Osypka ............ 607/117 |
| 2006/0052826 A1 | 3/2006 | Kim et al. |
| 2006/0052827 A1 | 3/2006 | Kim et al. |
| 2006/0052828 A1 | 3/2006 | Kim et al. |
| 2006/0052835 A1 | 3/2006 | Kim et al. |
| 2006/0052836 A1 | 3/2006 | Kim et al. |
| 2006/0052837 A1 | 3/2006 | Kim et al. |
| 2006/0052838 A1 | 3/2006 | Kim et al. |
| 2006/0052839 A1 | 3/2006 | Kim et al. |
| 2006/0052856 A1 | 3/2006 | Kim et al. |
| 2006/0064150 A1 | 3/2006 | Heist et al. |
| 2006/0089609 A1 | 4/2006 | Bleich et al. |
| 2006/0089696 A1 | 4/2006 | Olsen et al. |
| 2006/0094976 A1 | 5/2006 | Bleich |
| 2006/0095088 A1 | 5/2006 | DeRidder |
| 2006/0155344 A1 | 7/2006 | Rezai et al. |
| 2006/0161235 A1 | 7/2006 | King |
| 2006/0167525 A1 | 7/2006 | King |
| 2006/0195169 A1 | 8/2006 | Gross et al. |
| 2006/0200121 A1 | 9/2006 | Mowery |
| 2006/0206118 A1 | 9/2006 | Kim et al. |
| 2006/0241716 A1 | 10/2006 | Finch et al. |
| 2007/0043400 A1 | 2/2007 | Donders et al. |
| 2007/0060954 A1 | 3/2007 | Cameron et al. |
| 2007/0123954 A1 | 5/2007 | Gielen et al. |
| 2007/0179579 A1 | 8/2007 | Feler et al. |
| 2007/0213671 A1 | 9/2007 | Hiatt |
| 2007/0255366 A1 | 11/2007 | Gerber et al. |
| 2007/0270928 A1* | 11/2007 | Erlebacher ............ 607/126 |
| 2007/0276319 A1 | 11/2007 | Betts |
| 2008/0009927 A1 | 1/2008 | Vilims |
| 2008/0033431 A1 | 2/2008 | Jung et al. |
| 2008/0039916 A1 | 2/2008 | Colliou et al. |
| 2008/0103572 A1 | 5/2008 | Gerber |
| 2008/0103579 A1 | 5/2008 | Gerber |
| 2008/0103580 A1* | 5/2008 | Gerber ............ 607/149 |
| 2008/0119711 A1 | 5/2008 | Nikumb et al. |
| 2008/0154349 A1 | 6/2008 | Rossing et al. |
| 2008/0188916 A1 | 8/2008 | Jones et al. |
| 2009/0204173 A1 | 8/2009 | Fang et al. |
| 2010/0179562 A1 | 7/2010 | Linker et al. |
| 2011/0184486 A1 | 7/2011 | De Ridder |
| 2011/0257693 A1 | 10/2011 | Burdulis |
| 2011/0276056 A1 | 11/2011 | Grigsby et al. |
| 2012/0158094 A1 | 6/2012 | Kramer et al. |
| 2012/0197370 A1 | 8/2012 | Kim et al. |
| 2012/0277839 A1 | 11/2012 | Kramer et al. |
| 2012/0283697 A1 | 11/2012 | Kim et al. |
| 2012/0310140 A1 | 12/2012 | Kramer et al. |
| 2013/0165991 A1 | 6/2013 | Kim et al. |
| 2014/0200625 A1 | 7/2014 | Kim et al. |

FOREIGN PATENT DOCUMENTS

| | | |
|---|---|---|
| CN | 101678204 A | 3/2010 |
| EP | 0779080 A | 6/1997 |
| EP | 1304135 A2 | 4/2003 |
| JP | 03041191 B2 | 6/1991 |
| JP | H06-218064 A | 8/1994 |
| JP | 8500996 | 2/1996 |
| JP | 8080353 A | 3/1996 |
| JP | 10243954 A | 9/1998 |
| JP | 2004512105 | 4/2004 |
| JP | 2006523215 | 10/2004 |
| JP | 2005516697 | 6/2005 |
| JP | 2006508768 | 3/2006 |
| JP | 2008526299 | 7/2008 |
| JP | 2009539425 A | 11/2009 |
| JP | 2009539426 A | 11/2009 |
| WO | WO02096512 A1 | 12/2002 |
| WO | WO 03/018113 A1 | 3/2003 |
| WO | WO 03/043690 A1 | 5/2003 |
| WO | WO 03/063692 | 8/2003 |
| WO | WO 03/066154 A2 | 8/2003 |
| WO | WO 03/084433 A2 | 10/2003 |
| WO | WO 03/090599 A2 | 11/2003 |
| WO | WO 2005/092432 A1 | 10/2005 |
| WO | WO 2006/033039 A1 | 3/2006 |
| WO | WO 2006/084635 A2 | 8/2006 |

OTHER PUBLICATIONS

Kramer; U.S. Appl. No. 14/362,543 entitled "Neuromodulation of subcellular structures within the dorsal root ganglion," filed Jun. 3, 2014.

Horsch, S. et al. Epidural spinal cord stimulation in the treatment of severe peripheral arterial occlusive disease; Annals of Vascular Surgery; 8(5): 468-74. Sep. 1994.

Mayfield Clinic for Brain & Spine; printed from http://www.mayfieldclinic.com/PE-AnatSpine.htm (last updated Jan. 2013); 7 pages.

Medicinenet.com; Definition of Lateral; printed from http://www.medterms.com/script/main/art.asp?articlekey=6226 (on Jun. 4, 2014); 3 pages.

Linker et al.; U.S. Appl. No. 12/687,737 entitled "Stimulation leads, delivery systems and methods of use," filed Jan. 14, 2010.

Kishawi et al.; U.S. Appl. No. 12/730,908 entitled "Pain management with stimulation subthreshold to parasthesia," filed Mar. 24, 2010.

Brounstein et al.; U.S. Appl. No. 12/780,696 entitled "Methods, systems and devices for neuromodulating spinal anatomy," filed May 14, 2010.

Kocsis et al.; NR2B receptors are involved in the mediation of spinal segmental reflex potentials but not in the cumulative motoneuronal depolarization in vitro; Brain Research Bulletin, Elsevier Science Ltd.; vol. 64; No. 2; pp. 133-138; Aug. 30, 2004.

Lopez et al.; Excitatory and inhibitory effects of serotonin on spinal nociceptive reflexes are mediated by 5-HT2 and 5-HT1B receptors; (Database Biosis Biosciences information service, Philadelphia, PA, US, XP002567533, accession No. PREV200100573757); Abstract; 2001.

Dorsal Root Ganglion; www.biology-online.org/dDorsal_root_ganglion; downloaded Nov. 5, 2013; 4 pgs.

The Peripheral Nervous System; http://cnx.org/content/m44751/latest; downloaded Nov. 5, 2013; 7 pgs.

Abdulla et al.; Axotomy- and autotomy-induced changes in the excitability of rat dorsal root ganglion neurons; J Neurophysiol; 85(2): pp. 630-643; Feb. 2001.

Burton et al.; The organization of the seventh lumbar spinal ganglion of the cat; J Comp Neurol.; 149(2); pp. 215-232; May 15, 1973.

Ma et al.; Enhanced excitability of dissociated primary sensory neurons after chronic compression of the dorsal root ganglion in the rat; Pain; 113(1-2); pp. 106-112; Jan. 2005.

Myles et al.; Effects of different methods of peripheral nerve repair on the number and distribution of muscle afferent neurons in rat dorsal root ganglion; J Neurosurg; 77(3); pp. 457-462; Sep. 1992.

(56) References Cited

OTHER PUBLICATIONS

Prats-Galino et al.Prats; Representations of hindlimb digits in rat dorsal root ganglia; J Comp Neurol; 408(1); pp. 137-145; May 24, 1999.
Waxman et al.; Sodium channels, excitability of primary sensory neurons, and the molecular basis of pain; Muscle Nerve; 22(9); pp. 1177-1187; Sep. 1999.
Wessels et al.; A rostrocaudal somatotopic organization in the brachial dorsal root ganglia of neonatal rats; Clin Neurol Neurosurg; 95 Suppl; pp. S3-S11; 1993.
Wessels et al.; Evidence for a rostrocaudal organization in dorsal root ganglia during development as demonstrated by intra-uterine WGA-HRP injections into the hindlimb of rat fetuses; Brain Res Dev Brain Res; 54(2); pp. 273-281; Jul. 1, 1990.
Wessels et al.; Somatotopic organization in the sensory innervation of the rat hindlimb during development, using half dorsal root ganglia as subsegmental units; Eur J Morphol; 28(2-4); pp. 394-403; 1990.
Wessels et al.; The rostrocaudal organization in the dorsal root ganglia of the rat: a consequence of plexus formation?; Anat Embryol (Berl); 190(1); pp. 1-11; Jul. 1994.
Kim et al.; U.S. Appl. No. 12/369,706 entitled "Methods for stimulating a dorsal root ganglion," filed Feb. 11, 2009.
Nannini et al.; Muscle recruitment with intrafascicular electrodes; IEEE Trans on Biomedical Engineering; vol. 38; No. 8; pp. 769-776Aug. 1991.
Wedley et al. Handbook of Clinical Techniques in the Management of Chronic Pain. Taylor & Francis; pp. 17-19. Nov. 27, 1996.
Kishawi et al.; U.S. Appl. No. 13/753,326 entitled "Pain management with stimulation subthreshold to parasthesia," filed Jan. 29, 2013.
Burdulis; U.S. Appl. No. 13/975,083 entitled "Hard Tissue Anchors and Delivery Devices," filed Aug. 23, 2013.
Imran et al; U.S. Appl. No. 11/952,062 entitled "Implantable flexible circuit leads and methods of use," filed Dec. 6, 2007.
Burdulis, Albert; U.S. Appl. No. 11/952,065 entitled "Expandable stimulation leads and methods of use," filed Dec. 6, 2007.
Imran, Mir; U.S. Appl. No. 11/952,049, entitled "Grouped leads for spinal stimulation," filed Dec. 6, 2006.
Imran, Mir; U.S. Appl. No. 11/952,053 entitled "Delivery devices, systems and methods for stimulating nerve tissue on multiple spinal levels," filed Dec. 6, 2007.
Burdulis, Albert; U.S. Appl. No. 11/952,081 entitled "Hard tissue anchors and delivery devices," filed Dec. 6, 2007.
Advanced Neuromodulation Systems, Inc. (ANSI) Research Briefing dated Aug. 20, 2004 by Stephens Inc. Investment Bankers pp. 1-4.
Advanced Neuromodulation Systems, Inc. (ANSI) Research Bulletin dated Jul. 2, 2004 by Stephens Inc. Investment Bankers pp. 1-7.
Advanced Neuromodulation Systems, Inc. (ANSI) Research Bulletin dated Jul. 27, 2004 by Stephens Inc. Investment Bankers pp. 1-9.
Advanced Neuromodulation Systems, Inc. Equity Research dated Jan. 16, 2003 by Pacific Growth Equities pp. 1-8.
Alo, Kenneth M. 2002. New Trends in Neuromodulation for the Management of Neuropathic Pain. Neurosurgery. 50 (4): 690-703.
Aoki, Yasuhika et al. 2004. Distribution and Immunocytochemical Characterization of Dorsal Root Ganglion Neurons Innervating the Lumbar Intervertebral Disc in Rats: A Review. Life Sciences. 74 (21): 2627-2642.
Askar, Zahid, et al. 2003. Scott Wiring for Direct Repair of Lumbar Spondylolysis. Spine. 28 (4): 354-357.
Baba, Hiroshi et al. 1999. Peripheral Inflammation Facilitates A? Fiber-Mediated Synaptic Input to the Substantia Gelatinosa of the Adult Rat Spinal Cord. The Journal of Neuroscience. 19 (2): 859-867.
Bajwa, Zahid H. et al. 2001. Herpetic Neuralgia: Use of Combination Therapy for Pain Relief in Acute and Chronic Herpes Zoster. Geriatrics. 56 (12): 18-24.
Barendse, G.A. et al. 2001. Randomized Controlled Trial of Percutaneo Intradiscal Radiofrequency Thermocoagulation for Chronic Discogenic Back Pain: Lack of Effect From a 90-Second 70 C Lesion. Spine. 26 (3): 287-92. (Abstract Only).

Barlocher, C.B. et al. 2003. Kryorhizotomy: An Alternative Technique for Lumbar Medial Branch Rhizotomy in Lumbar Facet Syndrome. J Neurosurg. 98 (1): 14-20. (Abstract Only).
Blau, A. et al. 1997. Characterization and Optimization of Microelectrode Arrays for In Vivo Nerve Signal Recording and Stimulation. Biosens Bioelectron.12 (9-10): 883-92. (Abstract Only).
Boston Scientific A Neuromodulation Primer dated Jun. 9, 2004 in Medical Supplies and Devices, published by Susquehanna Financial Group, LLLP pp. 1-17.
Brammah, T.B. et al. 1994. Syringomyelia as a Complication of Spinal Arachnoiditis. Spine. 19 (22): 2603-5. (Abstract Only).
Braverman D.L. et al. 2001. Using Gabapentin to Treat Failed Back Surgery Syndrome Caused by Epidural Fibrosis: A Report of 2 Cases. Arch Phys Med Rehabil. 82 (5): 691-3. (Abstract Only).
Carlton, Susan M. et al. 2001. Tonic Control of Peripheral Cutaneo Nociceptors by Somatostatin Receptors. Journal of Neuroscience. 21 (11): 4042-4049.
Chaplan, S.R. et al. 1994. Quantitative Assessment of Tactile Allodynia in the Rat Paw. Journal of Neuroscience Methods. 53 (1): 55-63.
Cho, J. 1997. Percutaneo Radiofrequency Lumbar Facet Rhizotomy in Mechanical Low Back Pain Syndrome. Stereotact Funct Neurosurg. 68 (1-4): 212-7. (Abstract Only).
Crampon, M.-A. et al. 2002. Nerve Cuff Electrode With Shape Memory Alloy Armature: Design and Fabrication. Bio-Medical Materials and Engineering. 12 (4): 397-410.
Cuoco, Jr., Frank A. et al. 2000. Measurement of External Pressures Generated by Nerve Cuff Electrodes. IEEE Transactions on Rehabilitation Engineering. 8 (1): 35-41.
Cyberonics, Inc. Equity Research dated Jan. 16, 2003 by Pacific Growth Equities pp. 1-14.
Denny, N.M. et al. 2003. Evaluation of an Insulated Tuohy Needle System for the Placement of Interscalene Brachial Plex Catheters. Anaesthesia. 58 (6): 554-7. (Abstract Only).
Dreyfuss, Paul et al. 2000. Efficacy and Validity of Radiofrequency Neurotomy for Chronic Lumbar Zygapophysial Joint Pain. Spine. 25 (10): 1270-1277.
Dubuisson, D. 1995. Treatment of Occipital Neuralgia by Partial Posterior Rhizotomy at C1-3. J Neurosurg. 82 (4): 581-6. (Abstract Only).
Eschenfelder, Sebastian et al. 2000. Dorsal Root Section Elicits Signs of Neuropathic Pain Rather than Reversing Them in Rats With L5 Spinal Nerve Injury. Pain. 87 (2): 213-219.
Firth, Ava et al. 1999. Development of a Scale to Evaluate Postoperative Pain in Dogs. J Am Vet Med Assoc. 214 (5): 651-659.
Garcia Cosamalon, P. J. et al. 1991. Dorsal Percutaneo Radiofrequency Rhizotomy Guided With CT Scan in Intercostal Neuralgias. Technical note. Acta Neurochir (Wien). 109 (3-4): 140-1.
Giorgi, C. et al. 1984. Surgical Treatment of Glossopharyngeal Neuralgia and Pain From Cancer of the Nasopharynx. A 20-Year Experience. J Neurosurg. 61 (5): 952-5. (Abstract Only).
Gocer, A.I. et al. 1997. Percutaneo Radiofrequency Rhizotomy of Lumbar Spinal Facets the Results of 46 cases. Neurosurg Rev. 20 (2): 114-6. (Abstract Only).
Haller, H. et al. Treatment of Chronic Neuropathic Pain After Traumatic Central Cervical Cord Lesion with Gabapentin. Journal of Neural Transmission. 110 (9): 977-981.
Herron, L.D. 1989. Selective Nerve Root Block in Patient Selection for Lumbar Surgery: Surgical Results. J Spinal Disord. 2 (2): 75-9. (Abstract Only).
Higuchi, Yoshinori, et al. 2002. Exposure of the Dorsal Root Ganglion in Rats to Pulsed Radiofrequency Currents Activates Dorsal Horn Lamina I and II Neurons. Neurosurgery. 50 (4): 850-856.
Holsheimer, J. et al. 1995. Effects of Electrode Geometry and Combination on Nerve Fibre Selectivity in Spinal Cord Stimulation. Medical & Biological Engineering & Computing. 33 (5): 676-682.
Igarashi, T. et al. 2004. Lysis of Adhesions and Epidural Injection of Steroid/Local Anaesthetic During Epiduroscopy Potentially Alleviate Low Back and Leg Pain in Elderly Patients With Lumbar Spinal Stenosis. British Journal of Anaesthesia. 93 (2): 181-.
Julius, David et al. 2001. Molecular Mechanisms of Nociception. Nature. 413 (6852): 203-210.

(56) References Cited

OTHER PUBLICATIONS

Kanpolat, Yucel et al. 2001. Percutaneo Controlled Radiofrequency Trigeminal Rhizotomy for the Treatment of Idiopathic Trigeminal Neuralgia: 25-Year Experience with 1600 Patients. Neurosurgery. 48 (3): 524-534.
Kapadia, N.P. et al. 2000. Gabapentin for Chronic Pain in Spinal Cord Injury: A Case Report. Arch Phys Med Rehabil. 81 (10): 1439-41. (Abstract Only).
Kapoor, Vibhu et al. 2003. Refractory Occipital Neuralgia: Preoperative Assessment With CT-Guided Nerve Block Prior to Dorsal Cervical Rhizotomy. American Journal of Neuroradiology. 24 (10): 2105-10.
Karai, Laszlo et al. 2004. Deletion of Vanilloid Receptor 1—Expressing Primary Afferent Neurons for Pain Control. Journal of Clinical Investigation. 113 (9): 1344-1352.
Kline, David G. et al. 1998. Management and Results of Sciatic Nerve Injuries: a 24-Year Experience. Journal of Neurosurgery. 89 (1): 13-23.
Kobayashi, Shigeru et al. 2004. Pathology of Lumbar Nerve Root Compression Part 1: Intraradicular Inflammatory Changes Induced by Mechanical Compression. Journal of Orthopaedic Research. 22 (1): 170-179.
Kobayashi, Shigeru et al. 2004. Pathology of Lumbar Nerve Root Compression Part 2: Morphological and Immunohistochemical Changes of Dorsal Root Ganglion. Journal of Orthopaedic Research. 22 (1): 180-188.
Koszewski, W. et al. 2003. [The DREZ Lesion as an Effective Treatment for Chronic Hypothetically Post-Herpetic Neuropathic Pain. Case Report and Review of Literature]. Neurol Neurochir Pol. 37 (4): 943-53. (Abstract Only).
Lawrence, Stephen M. et al. 2002. Long-Term Biocompatibility of Implanted Polymer-Based Intrafascicular Electrodes. Journal of Biomedical Materials Research. 63 (5): 501-506.
Lee, In-Seop et al. 2002. Characterization of Iridium Film as a Stimulating Neural Electrode. Biomaterials. 23 (11): 2375-2380.
Lew, Henry L. et al. 2004. Preganglionic Approach to Transforaminal Epidural Steroid Injections. Am. J. Phys. Med. Rehabil. 83 (5): 378.
Maher, C.O. et al. 1999. Lateral Exit-Zone Stenosis and Lumbar Radiculopathy. J Neurosurg. 90 (1): 52-8. (Abstract Only).
Mailley, Sophie et al. 2004. Thin Film Platinum Cuff Electrodes for Neurostimulation: In Vitro Approach of Safe Neurostimulation Parameters. Bioelectrochemistry. 63: 359-364.
Masini, Michelle et al. 1996. Activated Pyrolytic Carbon Tip Pacing Leads: An Alternative to Steroid-Eluting Pacing Leads? PACE. 1: 1832-1835.
Medtronic, Inc. Equity Research dated Dec. 18, 2002 by Pacific Growth Equities pp. 1-20.
Medtronic. Analysis of Sales/Earnings-F1Q05: Many Gives and Takes in the Quarter dated Aug. 20, 2004 by Morgan Stanley pp. 1-25.
Methods of Placement of Neurostimulation Lead, Infusion, Catheter, and/or Sensor Via Peripheral Vasculature. From IP.com PriorArtDatabase—Apr. 10, 2003—#000012136 http://www.priorartdatabase.com/IPCCOM/000012136.
Modern Ideas: The Gate Control Theory of Chronic Pain. Spine-Health.com: Your Comprehensive Resource for Back Pain. http://www.spine-health.com/topics/cd/pain/chronic_pain_theories/chronic_pain_theory02.html (accessed Feb. 24, 2006).
Mond, Harry G. et al. 2004. Implantable Transveno Pacing Leads: The Shape of Things to Come. PACE. 27: 887-893.
Monti, Enrico. 2004. Peripheral Nerve Stimulation: A Percutaneo Minimally Invasive Approach. Neuromodulation. 7 (3): 193. (Abstract Only).
Naples, Gregory G. 1988. A Spiral Nerve Cuff Electrode for Peripheral Nerve Stimulation. IEEE Transactions on Biomedical Engineering. 35 (11): 905-916.
Narozny, Martin et al. 2001. Therapeutic Efficacy of Selective Nerve Root Blocks in the Treatment of Lumbar Radicular Leg Pain. Swiss Med Wkly. 131 (5-6): 75-80.

Nashold, Blaine S. et al. 1979. Peripheral Nerve Stimulation for Pain Relief Using a Multicontact Electrode System. Technical note. Journal of Neurosurgery. 51 (6): 872-873.
Nashold, Blaine S. et al. 1982. Long-Term Pain Control by Direct Peripheral-Nerve Stimulation. The Journal of Bone and Joint Surgery. 64 (1): 1-10.
Neumann, Simona et al. 2002. Regeneration of Sensory Axons Within the Injured Spinal Cord Induced by Intraganglionic cAMP Elevation. Neuron. 34 (6): 885-93.
Nielson, K.D. et al. 1976. Peripheral Nerve Injury From Implantation of Chronic Stimulating Electrodes for Pain Control. Surg Neurol. 5 (1): 51-3. (Abstract Only).
North, Richard B. et al. 1991. Dorsal Root Ganglionectomy for Failed Back Surgery Syndrome: A 5-Year Follow-Up Study. J Neurosurg. 74: 236-242.
North, Richard B. et al. 2000. Chapter 123: Current Concepts in the Neurosurgical Management of Persistent Pain (pp. 1634-1637). Operative Neurosurgical Techniques 4th Edition (Henry H. Schmidek et al. eds.). Philadelphia: W.B. Saunders Company.
Nygaard, Oystein P. et al. 1998. The Function of Sensory Nerve Fibers in Lumbar Radiculopathy: Use of Quantitative Sensory Testing in the Exploration of Different Populations of Nerve Fibers and Dermatomes. Spine. 23 (3): 348-352.
Obata, K. et al. 2004. Activation of Extracellular Signal-Regulated Protein Kinase in the Dorsal Root Ganglion Following Inflammation Near the Nerve Cell Body. Neuroscience. 126 (4): 1011-1021.
Obata, Koichi, et al. 2002. Expression of Neurotrophic Factors in the Dorsal Root Ganglion in a Rat Model of Lumbar Disc Herniation. Pain. 99 (1-2): 121-132.
Olby, Natasha J. et al. 2001. Development of a Functional Scoring System in Dogs With Acute Spinal Cord Injuries. Am J Vet Res. 62 (10): 1624-1628.
Parlier-Cuau, Caroline et al. 1999. Symptomatic Lumbar Facet Joint Synovial Cysts: Clinical Assessment of Facet Joint Steroid Injection After 1 and 6 Months and Long-Term Follow-Up in 30 Patients. Radiology. 210 (2): 509-513.
Pedrolli, C. et al. 1990. [Dorsolumbar Arachnoid Cysts. A Case Report]. Recenti Prog Med. 81 (11): 699-701. (Abstract Only).
Rodriguez, Francisco J. et al. 2000. Polyimide Cuff Electrodes for Peripheral Nerve Stimulation. Journal of Neuroscience Methods. 98 (2): 105-118.
Rokugo, Tomoyuki et al. 2002. A Histochemical Study of Substance P in the Rat Spinal Cord: Effect of Transcutaneo Electrical Nerve Stimulation. J Nippon Med Sch. 69 (5): 428-433.
Romero, E. et al. 2001. Neural Morphological Effects of Long-Term Implantation of the Self-Sizing Spiral Cuff Nerve Electrode. Medical & Biological Engineering & Computing. 39 (1): 90-100.
Rongstad, K. et al. 1996. Popliteal Sciatic Nerve Block for Postoperative Analgesia. Foot Ankle Int. 17 (7): 378-82. (Abstract Only).
Ruetten, S. et al. 2003. Endoscopic Surgery of the Lumbar Epidural Space (Epiduroscopy): Results of Therapeutic Intervention in 93 Patients. Minim Invasive Neurosurg. 46 (1): 1-4. (Abstract Only).
Sairyo, K. et al. 2003. A New Endoscopic Technique to Decompress Lumbar Nerve Roots Affected by Spondylolysis. Technical Note. J Neurosurg. 98 (3): 290-3. (Abstract Only).
Salame, K. et al. 2003. Surgical Treatment of Spasticity by Selective Posterior Rhizotomy 30 Years Experience. Isr Med Assoc J. 5 (8): 543-6. (Abstract Only).
Saris, S.C. et al. 1986. Sacrococcygeal Rhizotomy for Perineal Pain. Neurosurgery. 19 (5): 789-93. (Abstract Only).
Sauvage, P.J. et al. 2000. Intraspinal Synovial Cysts of the Lumbar Spine: Imaging Findings and Treatment by Percutaneo Steroid Injection. Review of 13 Cases. [Kystes Synoviaux Intraspinaux Lombaires: Imagerie et Traitement Par Infiltration. A Propos De.
Schwartzman, Robert J. et al. 2001. Neuropathic Central Pain: Epidemiology, Etiology, and Treatment Options. Arch Neurol. 58 (10): 1547-1550.
Sedan, R. et al. 1978. Therapeutic Electrical Neurostimulation. French Language Society of Neurosurgery—28th Annual Congress—Athens, May 29-30, 1978. Neurochirurgie. 24: 3-& Suppl. 1 (in French with English Summary pp. 121-125.

(56) References Cited

OTHER PUBLICATIONS

Sheth, Rishi N. et al. 2002. Mechanical Hyperalgesia After an L5 Ventral Rhizotomy or an L5 Ganglionectomy in the Rat. Pain. 96: 63-72.
Siddall, Philip J. et al. 2004. Persistent Pain as a Disease Entity: Implications for Clinical Management. Anesth Analg. 99: 510-20.
Silvers, H.R. 1990. Lumbar Percutaneo Facet Rhizotomy. Spine.15 (1): 36-40. (Abstract Only).
Slappendel, R. et al. 1997. The efficacy of Radiofrequency Lesioning of the Cervical Spinal Dorsal Root Ganglion in a Double Blinded Randomized Study: No difference Between 40 Degrees C and 67 Degrees C Treatments. Pain. 73 (2): 159-63. (Abstract Only).
Sluijter, Menno E. et al. 1998. The Effects of Pulsed Radiofrequency Fields Applied to the Dorsal Root Ganglion—A Preliminary Report. The Pain Clinic.11 (2): 109-117.
Smith, H.P. et al. 1981. Radiofrequency Neurolysis in a Clinical Model: Neuropathological Correlation. J Neurosurg. 55 (2): 246-53. (Abstract Only).
Spaic, M. et al. 1999. Drez Surgery on Con Medullaris (After Failed Implantation of Vascular Omental Graft) for Treating Chronic Pain Due to Spine (Gunshot) Injuries. Acta Neurochir(Wein). 141(12): 1309-1312.
Spaic, M. et al. 2002. Microsurgical DREZotomy for Pain of Spinal Cord and Cauda Equina Injury Origin: Clinical Characteristics of Pain and Implications for Surgery in a Series of 26 Patients. Acta Neurochir (Wien). 144 (5): 453-462.
Stanton-Hicks, M. et al. 1997. Stimulation of the Central and Peripheral Nervo System for the Control of Pain. Journal of Clinical Neurophysiology. 14 (1): 46-62.
Steinbok, P. et al. 1998. Complications After Selective Posterior Rhizotomy for Spasticity in Children With Cerebral Palsy. Pediatr Neurosurg. 28 (6): 300-13. (Abstract Only).
Stolker, Robert J. et al. 1994. The Treatment of Chronic Thoracic Segmental Pain by Radiofrequency Percutaneo Partial Rhizotomy. J Neurosurg. 80 : 986-992.
Strait, T.A. et al. 1981. Intraspinal Extradural Sensory Rhizotomy in Patients With Failure of Lumbar Disc Surgery. J Neurosurg. 54 (2): 193-6. (Abstract Only).
Taha, J.M. et al. 1995. Long-Term Results of Radiofrequency Rhizotomy in the Treatment of Cluster Headache. Headache. 35 (4): 193-6. (Abstract Only).
Taub, Arthur et al. 1995. Dorsal Root Ganglionectomy for Intractable Monoradicular Sciatica: A Series of 61 Patients. Stereotact Funct Neurosurg. 65 (1-4): 106-110.
Uematsu, Sumio. 1988. Chapter 106: Percutaneo Electrothermocoagulation of Spinal Nerve Trunk, Ganglion, and Rootlets (pp. 1207-1221). Operative Neurosurgical Techniques, Indications, Methods and Results 2nd edition. (Henry H. Schmidek et al. eds.). P.
Van Zundert, Jan et al. 2005. Pulsed Radiofrequency in Chronic Pain Management: Looking for the Best Use of Electrical Current. World Institute of Pain. 5 (2): 74-76.
Van De Kraats, Everine B. et al. 2004. Noninvasive Magnetic Resonance to Three-Dimensional Rotational X-Ray Registration of Vertebral Bodies for Image-Guided Spine Surgery. Spine. 29 (3): 293-297.
Van Kleef, M. et al. 1993. Effects and Side Effects of a Percutaneo Thermal Lesion of the Dorsal Root Ganglion in Patients with Cervical Pain Syndrome. Pain. 52 (1): 49-53.
Van Kleef, M. et al. 1996. Radiofrequency Lesion Adjacent to the Dorsal Root Ganglion for Cervicobrachial Pain: A Prospective Double Blind Randomized Study. Neurosurgery. 38 (6): 1127-31.
Van Kleef, Maarten et al. 1998. Chapter 160: Radiofrequency Lesions in the Treatment of Pain of Spinal Origin (pp. 1585-1599). Textbook of Stereotactic and Functional Neurosurgery 1st Edition. (Philip L. Gildenberg et al. eds.). New York: McGraw-Hill.
Van Zundert, J. et al. 2005. Pulsed and Continuo Radiofrequency Current Adjacent to the Cervical Dorsal Root Ganglion of the Rat Induces Late Cellular Activity in the Dorsal Horn. Anesthesiology. 102 (1): 125-31.
Vaughan, R. 1975. Percutaneo Radiofrequency Gangliotomy in the Treatment of Trigeminal Neuralgia and Other Facial Pain. Aust N Z J Surg. 45 (2): 203-7. (Abstract Only).
Viton, J.-M. et al. 1998. Short-Term Assessment of Periradicular Corticosteroid Injections in Lumbar Radiculopathy Associated With Disc Pathology. Neuroradiology. 40 (1): 59-62.
Viton, J.M. et al. 1998. Short-Term Evaluation of Periradicular Corticosteroid Injections in the Treatment of Lumbar Radiculopathy Associated With Disc Disease. Rev Rhum Engl Ed. 65 (3): 195-200. (Abstract Only).
Wagner, A.L. et al. 2002. Selective Nerve Root Blocks. Tech Vasc Interv Radiol. 5 (4): 194-200. (Abstract Only).
Weiner, Richard L. 2000. The Future of Peripheral Nerve Neurostimulation. Neurological Research. 22 (3): 299-304.
Weiner, Richard L. 2003. Peripheral Nerve Neurostimulation. Neurosurgery Clinics of North America. 14 (3): 401-408.
Weinstein, James et al. 1988. The Pain of Discography. Spine. 13(12):1344-8.
Wetzel, F. Todd et al. 1997. Extradural Sensory Rhizotomy in the Management of Chronic Lumbar Radiculopathy: A Minimum 2-Year Follow-up Study. Spine. 22 (19): 2283-2291.
Wetzel, F.T. 1992. Chronic Benign Cervical Pain Syndromes: Surgical Considerations. Spine. 17 (10): S367-74. (Abstract Only).
Wetzel, F.T. et al. 1992. The Treatment of Chronic Extremity Pain in Failed Lumbar Surgery. The Role of Lumbar Sympathectomy. Spine. 17 (12): 2367-8. (Abstract Only).
White, P.F. et al. 2003. The Use of a Continuo Popliteal Sciatic Nerve Block After Surgery Involving the Foot and Ankle: Does It Improve the Quality of Recovery? Anesth Analg. 97 (5): 1303-9. (Abstract Only).
Whitworth, Louis Anthony et al. 2002. Application of Spinal Ablative Techniques for the Treatment of Benign Chronic Painful Conditions. Spine. 27 (22): 2607-2612.
Wilkinson, H.A. et al. 2001. Sensory Ganglionectomy: Theory, Technical Aspects, and Clinical Experience. J Neurosurg. 95 (1): 61-6. (Abstract Only).
Wong, C.B. et al. 2002. Clinical Outcomes of Revision Lumbar Spinal Surgery: 124 Patient With a Minimum of Two Years of Follow-Up. Chang Gung Med J. 25 (3): 175-82. (Abstract Only).
Wright, Robert E. et al. 1998. Neurostimulation of the L2 Dorsal Root Ganglion for Intractable Disc Pain: Description of a Novel Technique. Presented at the IFESS.
Wu, Gang et al. 2001. Early Onset of Spontaneo Activity in Uninjured C-Fiber Nociceptors After Injury to Neighboring Nerve Fibers. Journal of Neuroscience. 21 (8): RC140.
Yamashita, Toshihiko et al. 2002. A Quantitative Analysis of Sensory Function in Lumbar Radiculopathy Using Current Perception Threshold Testing. Spine. 27 (14):1567-1570.
Yoshida, Hirotoshi et al. 1997. Lumbar Nerve Root Compression Caused by Lumbar Intraspinal Gas: Report of Three Cases. Spine.22 (3): 348-351.
Young, R.F. 1996. Chapter 161: Dorsal Rhizotomy and Dorsal Root Ganglionectomy (pp. 3442-3451). Neurological Surgery 4th Edition. (Julian R. Youmans ed.). Philadelphia: W.B. Saunders Company.
Kim et al; U.S. Appl. No. 12/051,770 entitled "Neurostimulation system," filed Mar. 19, 2008.

* cited by examiner

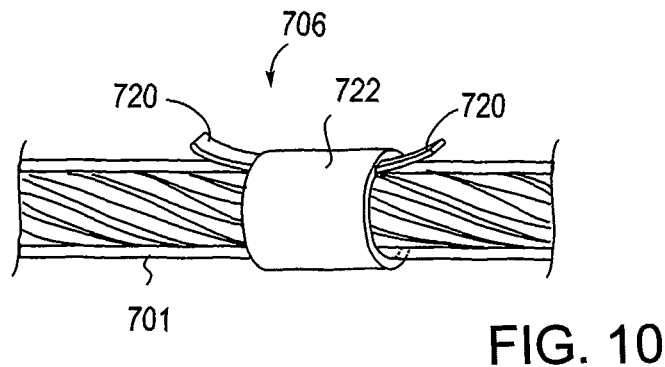
FIG. 10
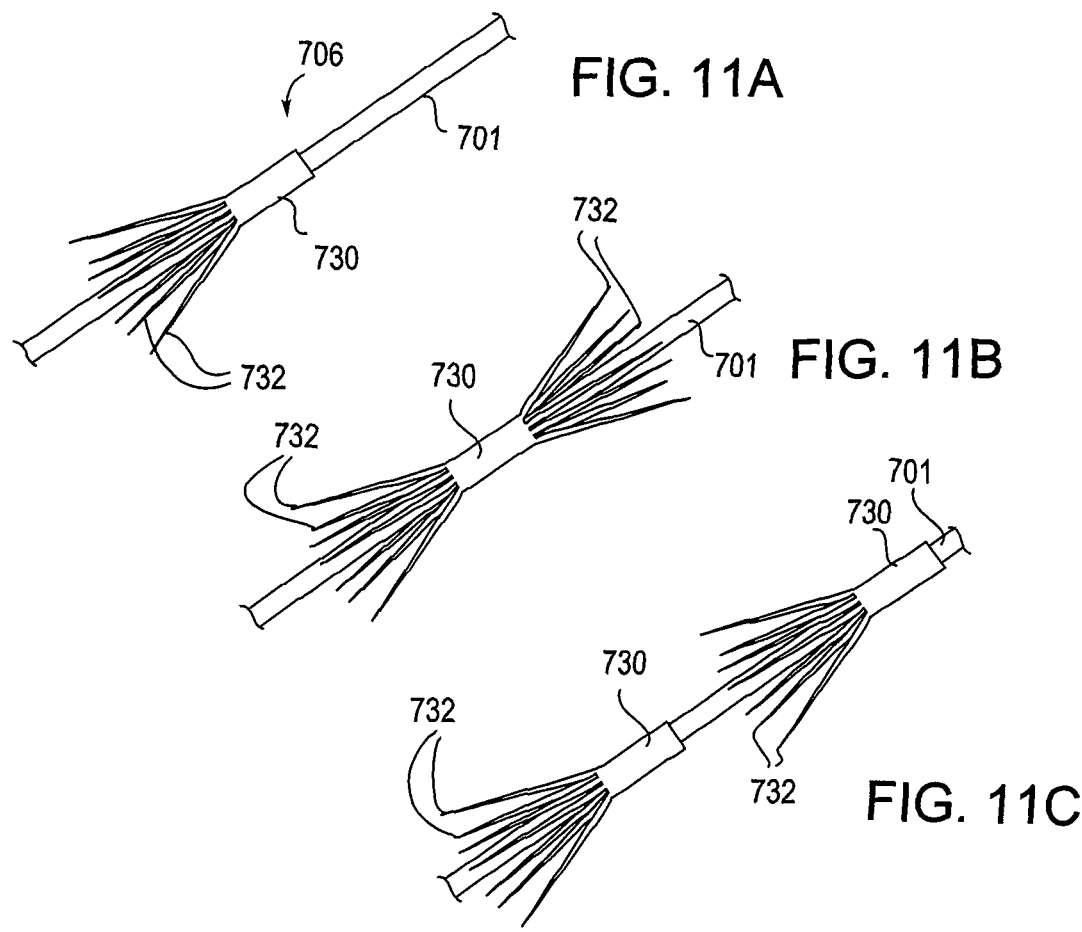
FIG. 11A
FIG. 11B
FIG. 11C

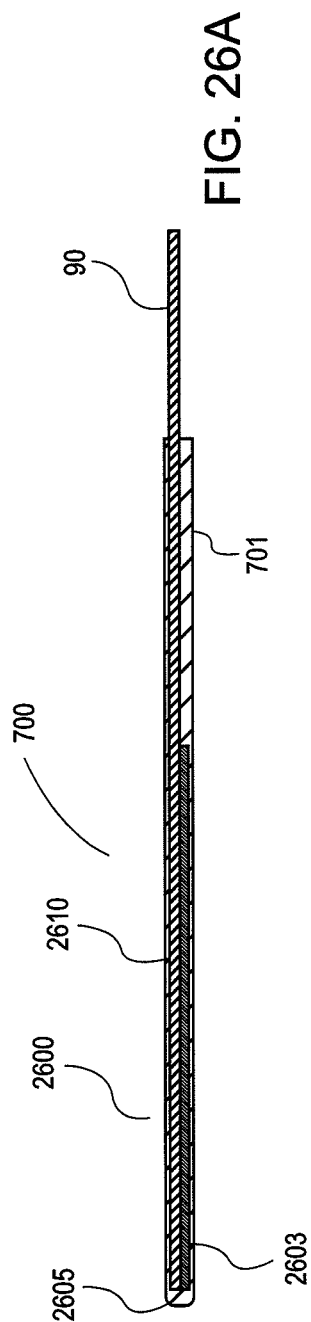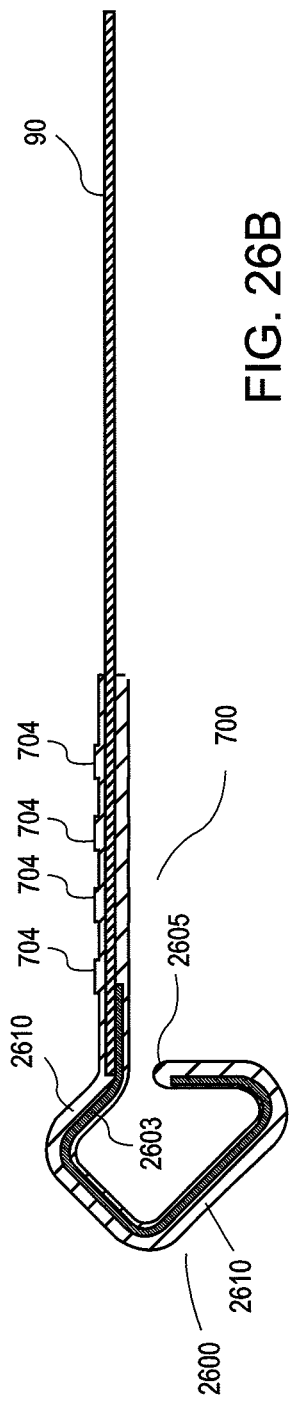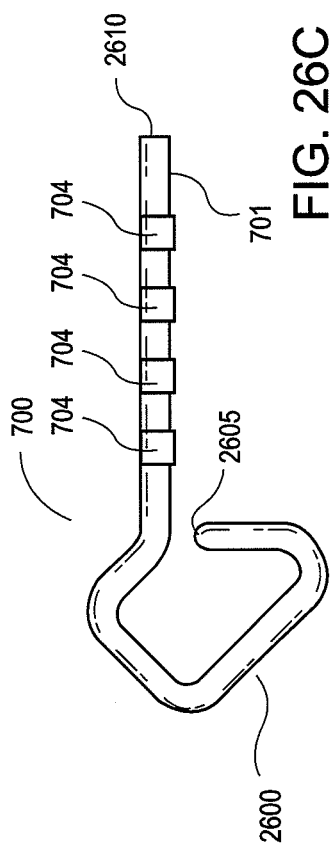

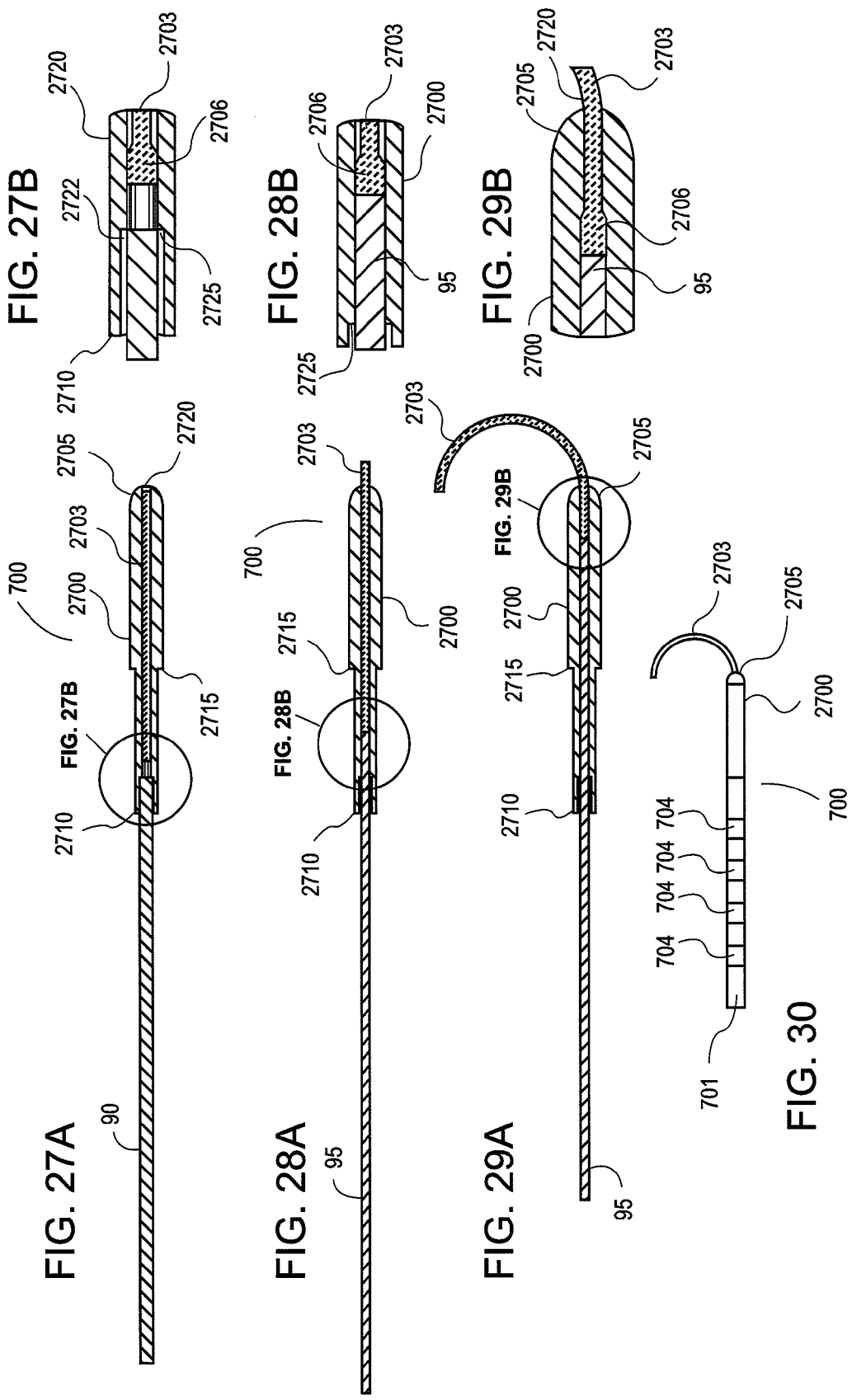

SUTURELESS LEAD RETENTION FEATURES

CROSS REFERENCE TO RELATED APPLICATIONS

This application claims priority to U.S. Provisional Application Ser. No. 60/898,342 filed on Jan. 29, 2007 entitled "Sutureless Lead Retention Features" and U.S. Provisional Application Ser. No. 60/998,722 filed on Oct. 12, 2007 entitled "Coiled Lead Retention Feature", each of these provisional patent applications are incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Electrical stimulation and drug delivery to portions of the anatomy, particularly the spinal anatomy and peripheral nervous system, often involve the implantation of one or more leads or delivery devices within the patient's body. The leads or delivery devices extend between the target anatomy and an implantable pulse generator (IPG) or drug reservoir which is typically implanted at a remote location. Precise positioning of the leads or delivery devices is desired to optimize treatment. Accuracy in administration of the drugs or stimulation to a particular target location can maximize beneficial effects of treatment and patient satisfaction. It is desired that such accuracy be maintained over time to ensure continued successful treatment.

For example, when implanting an epidural lead, a physician must surgically open the body tissue to the epidural space, and then insert the lead into the epidural space to the desired location. Fluoroscopy aids the physician, and trial and error tests of treatment define the desired location(s) for treatment. Once optimally positioned, it is desired to maintain the lead in place. Typically this is attempted by suturing the lead in place, such as by attaching a suture sleeve to the lead and suturing the sleeve to the surrounding tissue where the lead enters the epidural space. In addition, sutures are placed to prevent movement between the sleeve and the lead. The quality of the connection between the sleeve and lead depends on the tightness of the sutures and is highly variable. Such suturing is time consuming, tedious and subject to error. Further, any repositioning requires removal of the sutures and re-suturing. Also, such suturing is dependent on the quality and availability of suitable surrounding tissue and accessibility to the physician.

Unfortunately, leads have been known to move over time due to motion of the surrounding tissue after implantation. Therefore, attempts have been made to anchor the leads to resist migration. For example, when implanting an epidural lead, a physician inserts a lead into the epidural space and then typically sutures the lead to surrounding soft tissue. Pacemaker leads are typically anchored into soft tissue in or near the heart. And percutaneous catheters or peripherally inserted central catheters (PICC) are sutured to the skin outside of the body.

However, these methods are not applicable to minimally invasive procedures where the anchoring sites are not accessible by an open suture technique. In addition, such superficial suturing to soft tissue lacks stability in that soft tissue can stretch over time and during motion which may allow the lead to migrate. Thus, it is desired to provide mechanisms for anchoring leads, catheters and other devices within body tissue that are easy, efficient to use, reliable and allow anchoring in close proximity to the site of stimulation or drug delivery to enhance effectiveness and reduce the potential for migration. At least some of these objectives will be met by the present invention. It is desired to provide mechanisms for anchoring leads, catheters or other devices within body tissue that are easy and efficient to use, reliable, and adjustable. At least some of these objectives will be met by embodiments of the present invention.

SUMMARY OF THE INVENTION

In one embodiment, there is provided a system with a lead having a lead body and at least one electrode; and a retention feature disposed along the lead body proximal to the at least one electrode and configured to assist in atraumatically anchoring the lead to nearby tissue when the lead is positioned in the body.

In one aspect, the retention feature also includes a controllably deformable section.

In one aspect, the retention feature also includes a coiled retention feature.

In one aspect, the retention feature is movable into a first configuration for steering the lead and a second configuration to act as a retention feature.

In one aspect, the retention feature is reversibly movable into the first and the second configurations.

In one aspect, the retention feature comprises a gel or an expandable medium.

In one aspect, the retention feature is held into a non-bend configuration by a stylet and the retention feature moves into a retention configuration when the stylet is removed.

In one aspect, the retention feature is injected into a volume near or including a portion of the electrode or the targeted neural tissue.

In one aspect, the system also includes a port in the electrode body adapted and configured for injecting a gel or an expandable medium.

In one aspect, the retention feature is formed from or coated with a material selected to promote tissue in-growth.

In one embodiment, there is a provided system with a lead having a lead body and at least one electrode; and a coiled retention feature disposed along the lead body proximal to the at least one electrode and configured to assist in anchoring the lead to nearby tissue when the lead is positioned in a body.

In one aspect, the coiled retention feature is configured to atraumatically interact with the nearby tissue when the lead is in the body.

In one aspect, the diameter of the coiled retention feature is generally constant along the length of the coiled retention feature.

In one aspect, at least a portion of the coiled retention feature is imbedded into the lead body.

In one aspect, the lead body has a first portion with a first diameter and a second portion with a second diameter that is smaller than the first diameter; and wherein the coiled retention feature is disposed along the second portion.

In one aspect, the outer diameter of the coiled retention feature is about the same as the first diameter.

In one aspect, the outer diameter of the coiled retention feature is greater than the first diameter.

In one aspect, the coiled retention feature has an expanded state and wherein the diameter of the coiled retention feature in the expanded state is substantially equal to or less than the first diameter.

In one aspect, the lead is flexible along the lead body where the coiled retention feature is disposed.

In one aspect, the coiled retention feature is comprised of a flat wire having a rectangular cross-sectional shape.

In one aspect, the coiled retention feature is bioresorbable.

In one aspect, the coiled retention feature is configured to allow tissue in-growth.

In one aspect, the lead body is generally cylindrical and configured to be advanced through a lumen of a delivery device In one aspect, the nearby tissue is disposed within a back of a patient.

In one aspect, the nearby tissue is in the vicinity of a dorsal root ganglion.

In one aspect, only one end of the coiled retention feature is attached to the lead body.

In one aspect, the diameter of the coiled retention feature adjacent a proximal portion of the lead is larger than the diameter of the coiled retention feature adjacent a distal portion of the lead.

In one aspect, the diameter of the coiled retention feature adjacent a proximal portion of the lead is smaller than the diameter of the coiled retention feature adjacent a distal portion of the lead.

In one embodiment, there is a provided lead for stimulating a target neural tissue with an elongate body; at least one electrode disposed along the elongate body; and a passive retention feature disposed along the lead body proximal to the at least one electrode and configured to assist in anchoring the elongate body to tissue near the target neural tissue.

In one aspect, the passive retention feature assists in anchoring by friction.

In one aspect, at least a portion of the surface of the passive retention feature is treated to increase the friction between the surface of the passive retention feature and surrounding tissue when the lead is implanted in a body.

In one aspect, the passive retention feature assists in anchoring by tissue ingrowth.

In one aspect, the passive retention feature is disposed along the lead body in a location so as to assist in anchoring to non-neural tissue while the at least one electrode stimulates the target neural tissue.

In one aspect, the target neural tissue comprises a dorsal root ganglion.

In one aspect, the passive retention feature comprises a coil.

In one aspect, the coil is disposed substantially coaxially with the elongate body.

In one aspect, the passive retention feature is fixed in relation to axial movement along the lead body.

In one aspect, a distal-most end of the passive retention feature is disposed approximately 5 mm to 2 cm proximally of a proximal-most electrode of the at least one electrode.

In one aspect, the passive retention feature comprises a braided structure configured to buckle in a pre-defined manner.

In one embodiment, there is a system comprising a lead having a lead body and at least one electrode; and at least one retention feature disposed on the lead body, wherein the retention feature comprises at least one projection configured to assist in anchoring the lead to nearby tissue.

In one aspect, the nearby tissue is disposed within a back of a patient.

In one aspect, the nearby tissue is in the vicinity of a dorsal root ganglion.

In one embodiment, there is a retention feature comprising a tubular structure mountable on a lead body; and at least one projection which is extendable radially outwardly.

In one aspect, the tubular structure is mountable at a location along the lead body which is distal to a distal-most electrode configured to provide stimulation.

In one aspect, the tubular structure is mountable at a location along the lead body which is proximal to a proximal-most electrode configured to provide stimulation.

In one aspect, the at least one projection is comprised of a resorbable material.

In one aspect, the at least one projection is extendable so as to resist motion of the lead body in multiple planes or directions.

In another embodiment, there is a system comprising a body having a first portion with a first diameter and a second portion having a second diameter, wherein the second diameter is smaller than the first diameter; and a coil disposed around the second portion.

In one aspect, the coil has an expanded state and wherein the diameter of the coil in the expanded state is substantially equal to or less than the first diameter.

In one aspect, the coil is configured to allow tissue ingrowth.

In one aspect, the cylindrical body is advanceable through a lumen of a delivery device.

Still other additional embodiments are possible from combinations of the various embodiments and aspects described above.

BRIEF DESCRIPTION OF THE DRAWINGS

FIG. 10 illustrates a retention feature comprising a pre-formed projection.

FIGS. 11A-11C illustrate retention features comprising sleeves having at least one fanned end.

FIG. 26A illustrates a section view of a normally bend lead straightened by a stylet.

FIGS. 26B and 26C illustrate section and perspective views, respectively, of the lead in FIG. 26A with the stylet removed;

FIG. 27A illustrates a section view of a lead distal end on a stylet.

FIG. 27B illustrates an enlarged view of a portion of the embodiment of FIG. 27A.

FIG. 28A illustrates a section view of a lead distal end with a push rod engaged with a retention feature.

FIG. 28B illustrates an enlarged view of a portion of the embodiment of FIG. 27A.

FIG. 29A illustrates a section view of a lead distal end with a push rod engaged to push a retention feature out the lead distal end. FIG. 29B is an enlarged view of a portion of the embodiment of FIG. 29A.

FIG. 30 illustrates a perspective view of the lead in FIGS. 29A and 29B;

DETAILED DESCRIPTION OF THE INVENTION

A variety of retention features are provided for anchoring or retaining leads, catheters or other devices in desired positions within the body. In preferred embodiments, the retention features are sutureless so that the lead or catheter is held in place by the retention feature itself, without the need for suturing the retention feature to the surrounding tissue. This assists in ease of use, reduction of procedure time, and ability to anchor in areas which are not as readily accessible to the physician, such as by direct access with needle and suture. Likewise, the retention features are typically self-actuating or self-expanding, allowing the retention feature to deploy by spring force or without additional manipulation.

Figure 1A:
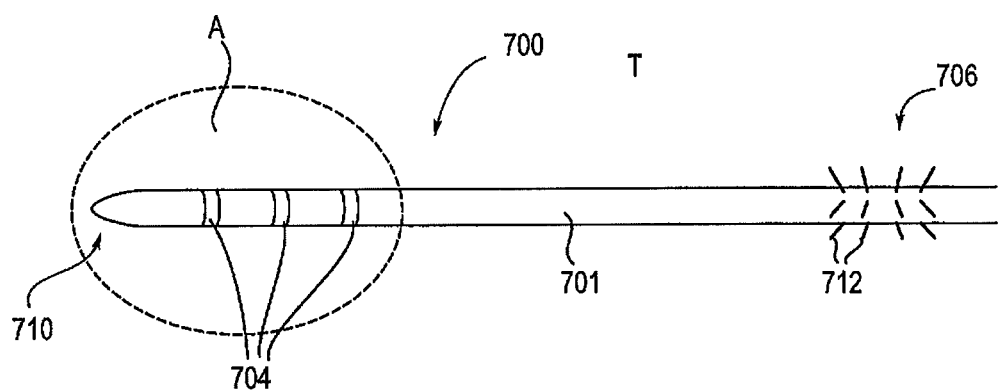
FIGS. 1A-1B illustrate an embodiment of a lead having a retention feature in various positions along the lead body.
Figure 1B:
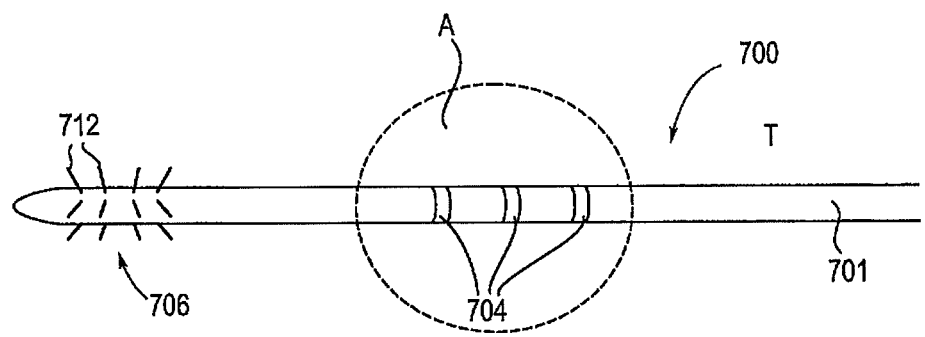

FIGS. 1A-1B illustrates an example lead 700 having a lead body 701, at least one electrode 704 thereon and at least one retention feature 706. The leads 700 are shown implanted within tissue T so that the electrodes 704 are positioned so as to stimulate a target area A of the tissue T. In FIG. 1A, the electrodes 704 are disposed near a distal end 710 of the lead body 701 and the retention feature 706 is disposed proximal to the electrodes 704. In FIG. 1B, the retention feature 706 is disposed proximal to the electrodes 704. Thus, the lead 700 can optionally be positioned to stimulate a target area A that does not include suitable anchoring tissue since the lead 700 will be retained outside of the target area A, on either or both sides of target area A. This allows a greater flexibility in placement of the lead 700.

In some embodiments, the retention feature 706 is adjustable along the length of the lead 700 to allow optimal positioning of the retention feature 706. In other embodiments, the retention feature 706 is fixed in place at a commonly desired location. Or, a plurality of retention features 706 may be fixed in place along the length of the lead 700 so that retention features 706 aligning with suitable tissue for anchoring are used to retain the lead in place. It may be appreciated that in any embodiment, a plurality of retention features 706 may be present at any intervals along its length.

In this embodiment, the retention feature 706 comprises a plurality of projections 712 which extend radially outwardly from the lead body 701. The projections 712 engage the surrounding tissue T, anchoring the lead 700 to the tissue T, such as by frictional force. Such projections 712 may be comprised of fibers, filaments, wires, sutures, threads, polymers or other material. Typically, the projections 712 have a hair-like or whisker-type shape, such as an elongate shaft or rod. However, the projections 712 may have any suitable shape, length, or diameter. The tips of the projections 712 may be blunt or sharpened, or have other shapes, such as barbed or fish-hooked. Further, any number of projections 712 may be present and the projections may vary within each retention feature 706. The projections 712 may extend at any angle or a plurality of angles from the lead body 701 so as to resist movement in a variety of directions or planes. During delivery, the projections 712 are covered by a sheath, delivery catheter or other suitable device. The lead 700 is advanced to a desired position and the sheath is withdrawn allowing the projections 712 to extend radially outwardly.

Figure 2:
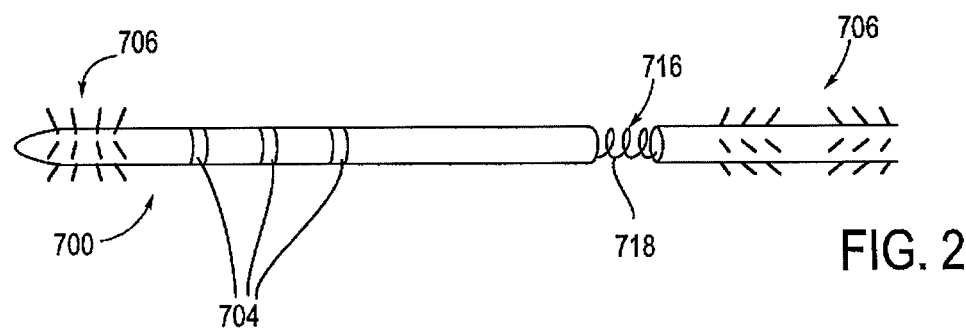
FIG. 2 illustrates an embodiment of a lead having a strain relief and multiple retention features.

FIG. 2 illustrates an embodiment of a lead 700 having at least one retention feature 706. Here, retention features 706 are shown proximal and distal to the electrodes 704. In addition, the lead 700 includes a strain relief 716. In this embodiment, the strain relief 716 comprises a coil 718 disposed proximal to the electrodes 704 which joins two portions of the lead 700. Thus, in the instance of tugging or motion of the lead 700 from its proximal end, such motion will be absorbed by the coil 718 leaving the distal end of the lead 700 stabilized. The distal end is additionally anchored in place by the distally located retention feature 706.

Figure 3A:
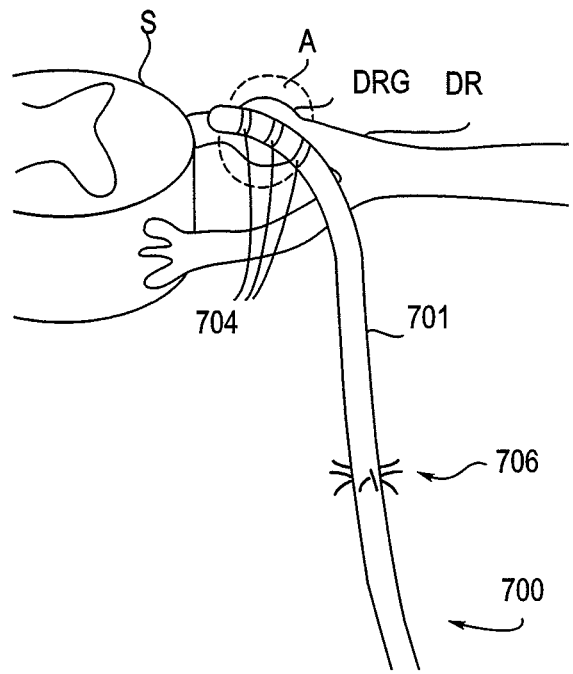
FIGS. 3A-3B illustrate implantation of leads wherein the target area for treatment comprises the dorsal root ganglion.
Figure 3B:
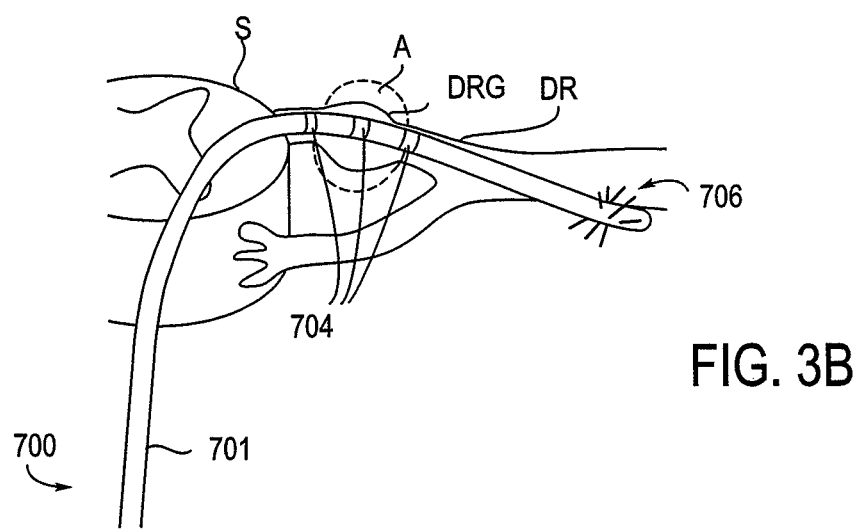

Although the retaining systems 706 of the present invention may be used for implanting a lead or catheter in any tissue, the retaining systems 706 are particularly suitable for implantation of leads or catheters treating the spinal anatomy. FIGS. 3A-3B illustrate implantation of leads 700 wherein the target area A for treatment comprises the dorsal root ganglion DRG. FIG. 3A illustrates an antegrade approach to the DRG from outside of the spinal column, such as from a side, lateral or percutaneous approach. It may be appreciated that a retrograde approach may alternatively be used. The lead 700 is positioned such that the electrodes 704 are near the DRG, and the lead body 701 extends away from the spinal column S for implantation within the tissues of the back, side or buttocks. In this embodiment, the lead 700 includes a retention feature 706 disposed along the lead body 701 to assist in anchoring the lead body 701 within the tissue during implantation. As shown, the retention feature 706 is disposed proximal to the electrodes 704 at a location that allows engagement with supportive tissue that can withstand frictional forces. Anchoring at such a location allows the distal end of the lead 700 to reside within more sensitive anatomy, near the DRG, without anchoring forces and disruption by movement.

FIG. 3B illustrates an antegrade epidural approach to a dorsal root and DRG between an articulating process (not shown) and the vertebral body (not shown). It may be appreciated that a retrograde approach may alternatively be used. The lead 700 is positioned such that the electrodes 704 are near the DRG, and the lead body 701 extends along the spinal column S. In some instances, it is not desired to anchor within the spinal column S. Thus, in this embodiment the lead 700 includes a retention feature 706 disposed near the distal end of the lead 701 to assist in anchoring the lead body 701 to tissue beyond the DRG that can withstand anchoring forces.

Embodiments of retention features are provided for anchoring or retaining leads, catheters or other devices in desired positions within the body. In preferred embodiments, the retention features are sutureless so that the lead or catheter is held in place by the retention feature itself, without the need for suturing the retention feature to the surrounding tissue. This assists in ease of use, reduction of procedure time, and ability to anchor in areas which are not as readily accessible to the physician, such as areas that are accessible by minimally invasive methods.

Figure 4:
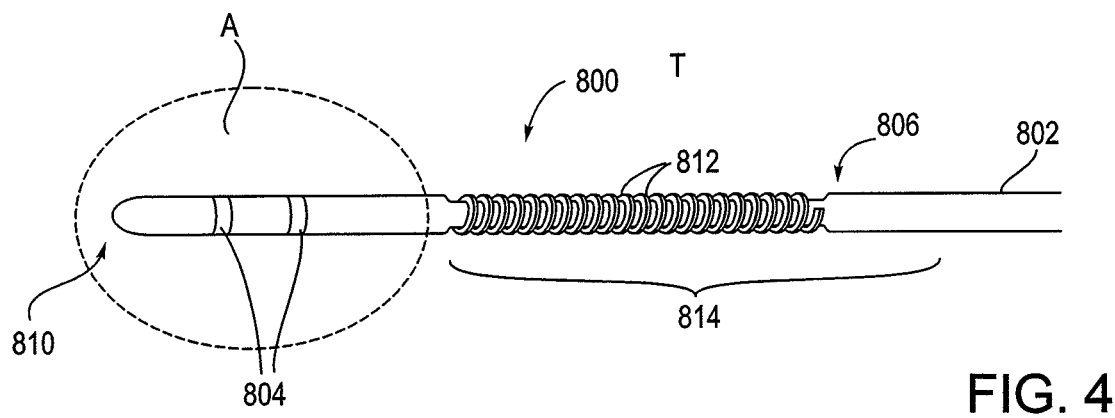
FIG. 4 illustrates an embodiment of a lead having a retention feature of the present invention.

FIG. 4 illustrates an example lead 800 having a lead body 802, at least one electrode 804 thereon and at least one retention feature 806. The lead 800 is shown implanted within tissue T so that the at least one electrode 804 is positioned so as to stimulate a target area A of the tissue T. Referring to FIG. 4, the electrodes 804 are disposed near a distal end 810 of the lead body 802 and the retention feature 806 is disposed proximal to the electrodes 804. Thus the lead 800 can optionally be positioned to stimulate a target area A that does not include suitable anchoring tissue since the lead 800 will be retained outside of the target area A, on either or both sides of target A. However, it may be appreciated that the retention feature 806 may be disposed in close proximity to the target area A.

In this embodiment, the retention feature 806 comprises a coil 812 wrapped around a section 814 of the lead body 802 having a reduced diameter. In some embodiments, the section 814 has a diameter that is sufficiently reduced to allow the coil 812 to be aligned with the outer diameter of the remainder of the lead body 802. Thus, the overall diameter of the lead body 802 is substantially uniform along its length, including along the section 814. However it may be appreciated that the section 814 may have any suitable diameter so as to position the coil in a desirable arrangement. For example, in some embodiments, the coil 812 is imbedded into the lead body 802 in the section 814. Thus, the section 814 of the lead body 802 may be indented in the areas that the coil 812 is imbedded creating a reduced diameter in some locations. Such imbedding typically fuses the coil 812 to the lead body 802 along the length of the coil 812.

Figure 5:
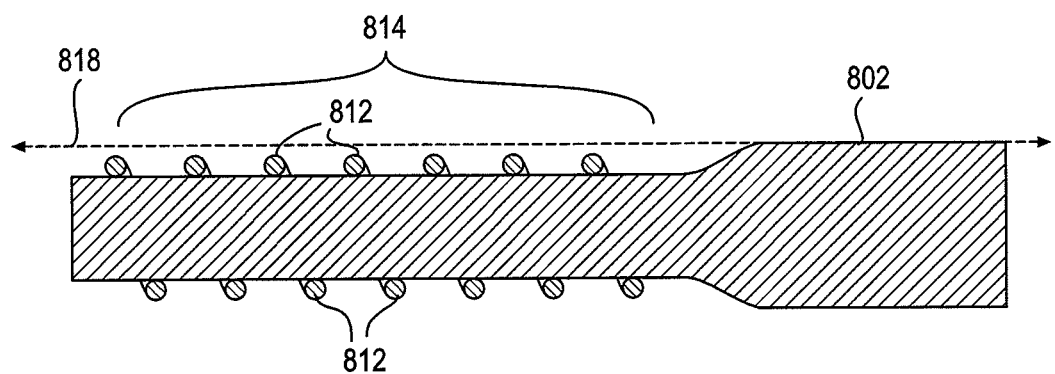
FIG. 5 provides a length-wise cross-sectional view of a portion of a lead body of FIG. 4.

FIG. 5 provides a length-wise cross-sectional view of a portion of the lead body 802, including a portion of the section 814 having a reduced diameter. As shown, the section 814 has a diameter that is sufficiently reduced to allow the coil 812 to be aligned with the outer diameter of the remainder of the lead body 802 (as indicated by dashed line 818).

The coil 812 may be anchored at each of its ends to the lead body 802. Alternatively, the coil 812 may be anchored at one end. The coil 812 provides friction with the tissue T due to the geometry of the coil and therefore initial fixation. Over time, the tissue T grows into and around the coil 812 for long term anchoring. Thus, coil 812 is a passive retention feature.

Figure 6:
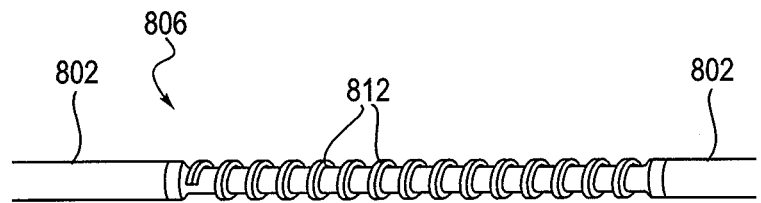
FIG. 6 illustrates an embodiment wherein the coil is comprised of a flat wire having a rectangular cross-sectional shape.

The coil 812 may be comprised of any suitable material including metal, polymer, elastic or superelastic materials and bioresorbable materials. Bioresorbable materials may enhance short term fixation yet allow increased ease in removability in the long term. Likewise, the coil 812 may be of any suitable length and may have any suitable spacing of coil turns. The coil turns may be selected to be spaced apart about a distance equal to the width of the wire used to form the coil. Further, the coil 812 may have any suitable cross-sectional shape, including round, square, rectangular, triangular, trapezoidal, etc. For example, FIG. 6 illustrates an embodiment wherein the coil 812 is comprised of a flat wire having a rectangular cross-sectional shape. Such a shape may increase frictional geometry by providing a larger surface area in contact with the surrounding tissue T during initial fixation.

Figure 7:
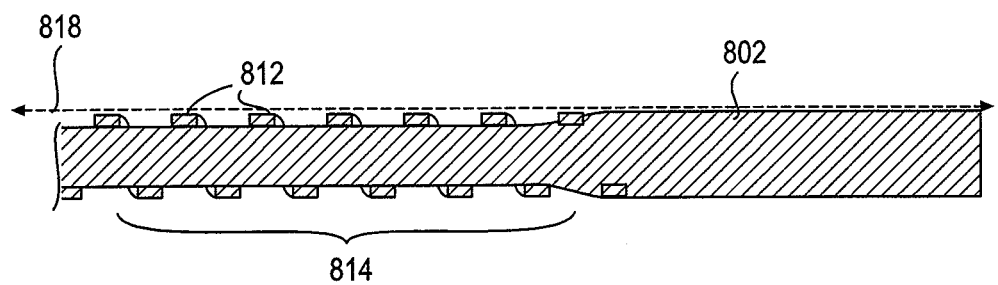
FIG. 7 provides a length-wise cross-sectional view of a portion of the lead body of FIG. 6.

FIG. 7 provides a length-wise cross-sectional view of a portion of the lead body 802 of FIG. 6, including a portion of the section 814 having a reduced diameter. As shown, the section 814 has a diameter that is sufficiently reduced to allow the coil 812 to be aligned with the outer diameter of the remainder of the lead body 802 (as indicated by dashed line 818).

The substantially uniform profile of the lead body 802, including the retention feature 806, allows delivery of the lead 800 through a needle or other minimally invasive delivery device. Further, the retention feature 806 does not require complex deployment methods.

The coiled design of the retention feature 806 allows the lead body 802 to bend at the site of fixation. Therefore, the lead 800 may be placed in a variety of anatomical areas, including along tortuous pathways. Further, placement of lead 800 may be determined independently of where the retention features 806 may reside along the tissue pathway since the retention features 806 do not limit the flexibility of the lead body 802. Such flexibility also reduces any possibility of kinking.

The coiled design of the retention feature 806 also allows maximal frictional fixation to the surrounding tissue while allowing a physician to reposition or remove the lead 800 without excessive damage to the surrounding tissue.

In some instances, the coil 812 may act as a suspension for the lead 800. For example, the coil 812 may be attached to the lead body 802 at each of its ends, allowing the center portion of the coil 812 to slide along the lead body 802. After tissue begins to grow into the coil 812, the lead body 802 may maintain some of such slidability. Thus, when migration forces are applied to the lead body 802 the lead body 802 may move within the limits of the spring constant of the coil 812 yet return to the passive position upon recoil.

Figure 8:
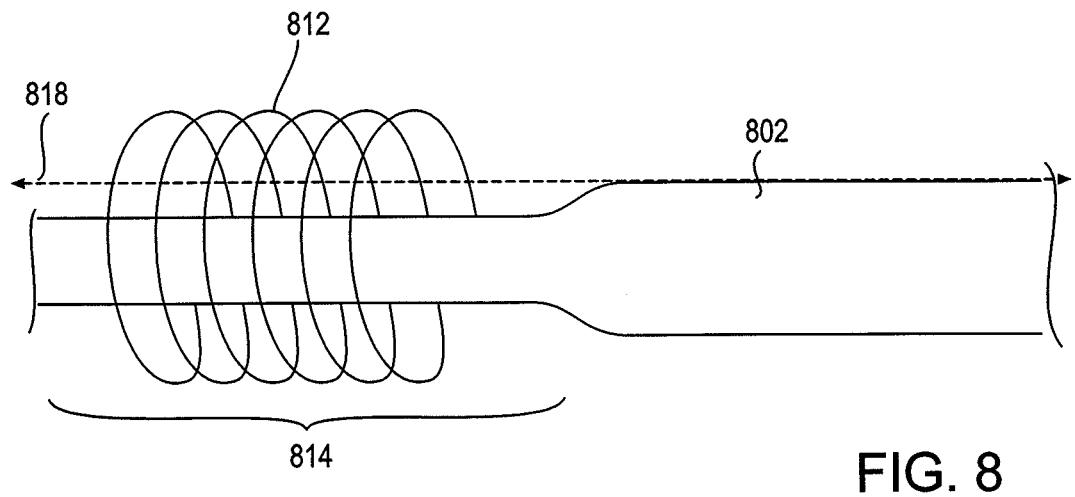
FIG. 8 illustrates an embodiment wherein the coil is expandable beyond the diameter of the lead body.

It may be appreciated that the present invention includes alternative embodiments of the retention feature 806 described above. For example, in some embodiments the coil 812 is expandable beyond the diameter of the lead body 802, as illustrated in FIG. 8. As shown, the section 814 has a diameter that is reduced, however the coil 812 is expandable beyond the outer diameter of the remainder of the lead body 802 (as indicated by dashed line 818). Thus, the reduced diameter of the section 814 allows the coil 812 to be condensed and optionally flush with the diameter of the remaining lead body 802 during delivery, such as for insertion through a needle, yet allows the coil 812 to expand to a desired dimension after delivery.

It may be appreciated that the coil 812 may be formed in a large diameter and twisted to reduce its diameter for delivery. The coil 812 may be held in the twisted configuration by a removable sheath or outer construct. Once the lead 800 is desirably placed, the construct is then removed, allowing the coil 812 to expand to its original larger shape for anchoring purposes.

The coil retention features described illustrated in FIGS. 4-8 may be modified to have coils with different diameters, a different number of coils or a different coil placement along the lead body and with regard to the electrodes 704.

Figure 9A:
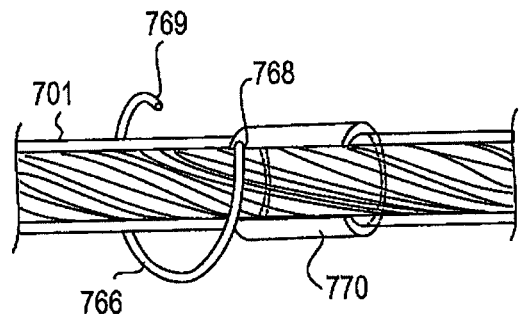
FIGS. 9A-9C illustrate retention features having a coil shape.
Figure 9B:
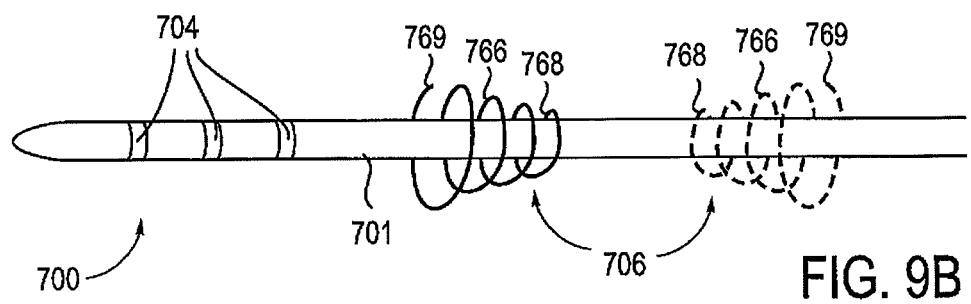
Figure 9C:
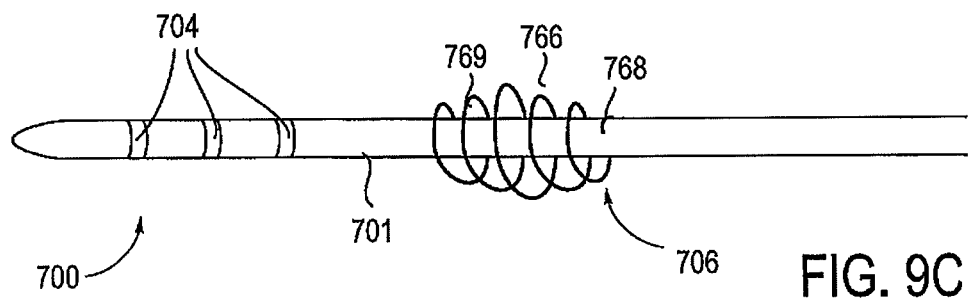

FIGS. 9A-9C illustrate embodiments of a retention feature 706 comprising one or more coils 766 mounted on a lead body 701. The coil 766 may be comprised of any suitable material including metal, polymer, elastic or superelastic materials. FIG. 9A illustrates a coil 766 which is fixedly or slidably attached to the lead body 701 at a first end 768 and coils around the lead body 701 to a second end 769 which is free and extended. The first end 768 may be attached to the lead body 701 by means of a cuff 770 which may bond the first end 768 to the lead body 701 or may be fixed to the first end 768 and capable of moving relative to the lead body 701. FIG. 9B illustrates a coil 766 which spirals from the first end 768 to a progressively larger diameter toward the second end 769, forming a funnel-type shape. During delivery, the coil 766 is covered by a sheath, delivery catheter or other suitable device. The coil 766 is pressed or coiled up to a low profile for covering. The lead 700 is advanced to a desired position and the sheath is withdrawn allowing the coil 766 to be revealed and recoil toward its original shape. The coil 766 provides resistance to movement of the lead body 701 in relation to the surrounding tissue, such as by providing friction. Further, the lead body 701 may be rotated to engage or penetrate the free second end 769 of the coil 766 into the surrounding tissue to anchor the lead body 701 during relative motion. It may be appreciated that a plurality of coils 766 may be disposed along the lead body 701. For example, an additional coil 766 is illustrated in dashed line facing an opposite direction wherein together the coils 766 provide migration resistance in both directions. FIG. 9C illustrates a coil 766 wherein both ends 768, 769 are fixedly or slidably attached to the lead body 701. Here, the coil 766 portion between the ends 768, 769 has a larger diameter and extends outwardly. Thus, this extending portion engages the surrounding tissue, anchoring the lead 700 in place.

The various coiled retention features described herein provide a system including a lead having a lead body and at least one electrode; and a retention feature disposed along the lead body proximal to the at least one electrode and configured to assist in atraumatically anchoring the lead to nearby tissue when the lead is positioned in the body. As shown in the embodiments of FIGS. 4-9C, the retention feature can be a controllably deformable section. More specifically, the retention includes a coiled retention feature. The coiled retention feature may be positioned as illustrated or on any location on the lead body proximal to the distal end of the lead body. The coiled retention feature may extend beyond the distal end of the lead body or the coiled retention feature may span a portion of the lead body where the entirely of the span is proximal to the distal end of the lead body The various embodiments illustrated and described in FIGS. 4-9C provide a system including a lead having a lead body and at least one electrode; and a coiled retention feature disposed along the lead body proximal to the at least one electrode and configured to assist in anchoring the lead to nearby tissue when the lead is positioned in a body. In general, these coiled retention features are configured to atraumatically interact with the nearby tissue when the lead is in the body. The nearby tissue is disposed within a back of a patient and/or is in the vicinity of a dorsal root ganglion or other targeted neural tissue locations. In general with all of these embodiments, the lead is flexible along the lead body where the coiled retention feature is disposed. In general, the coiled retention features described herein may be configured to allow tissue in-growth and/or be bioresorbable. In some coiled retention lead embodiments, the lead body along with the coiled retention feature is generally cylindrical and configured to be advanced through a lumen of a delivery device. In some embodiments, only one end of the coiled retention feature is attached to the lead body.

In the embodiments of FIGS. 4-7, the diameter of the coiled retention feature is generally constant along the length of the coiled retention feature. As best seen in FIGS. 6 and 7, the coiled retention feature may include a flat wire having a rectangular cross-sectional shape. At least a portion of the coiled retention feature is imbedded into the lead body as shown, for example, in FIG. 7. In one alternative, the lead body has a first portion with a first diameter and a second portion with a second diameter that is smaller than the first diameter; and wherein the coiled retention feature is disposed along the second portion as illustrated, for example, in FIGS. 4 and 5. Additionally, FIGS. 4 and 5 illustrate one way how the outer diameter of the coiled retention feature is about the same as the first diameter. FIGS. 4 and 5 also illustrate the case with the coiled retention feature having an expanded state and wherein the diameter of the coiled retention feature in the expanded state is substantially equal to or less than the first diameter.

In contrast, FIGS. 8, 9A, 9B and 9C illustrate embodiments where the outer diameter of the coiled retention feature is greater than the first diameter. Moreover, in some embodiments, the diameter of the coiled retention feature adjacent a proximal portion of the lead is larger than the diameter of the coiled retention feature adjacent a distal portion of the lead. Additionally or alternatively, the diameter of the coiled retention feature adjacent a proximal portion of the lead is smaller than the diameter of the coiled retention feature adjacent a distal portion of the lead.

Other alternative retention features are possible. Various other retention features may also be used to prevent or reduce lead migration.

FIG. 10 illustrates another embodiment of a retention feature 706 mounted on a lead body 701. In this embodiment, the retention feature 706 comprises one or more pre-formed projections 720 affixed to the lead body 701 by a cuff 722, and/or adhesive, and/or other affixing mechanisms. Example cuff 722 material includes shrink tubing. Example projection 720 material includes nitinol, or other metal, or preformed polymer. The projections 720 have a protruding shape, such as a curved or semi-circular shape, so as to protrude radially outwardly from the lead body 701. Prior to deployment, the pre-formed projections 720 are held along the lead body 701 by an external sheath or delivery device. Retraction of the sheath or delivery device exposes the pre-formed projections 720 allowing the projections 720 to recoil radially outwardly. Thus, the projections 720 extend into the surrounding tissue, resisting movement of the lead body 701 in relation to the tissue thereby anchoring the lead 700. The projections 720 may have any suitable size, shape and dimension, including a flat strip or elongate shaft. The tips of the projections 720 may be blunt or sharpened, or have other shapes, such as barbed or fish-hooked. Further, any number of projections 720 may be present and the projections may vary within each retention feature 706. The projections 720 may extend at any angle or a plurality of angles from the lead body 701 so as to resist movement in a variety of directions.

FIGS. 11A-11C illustrate additional embodiments of retention features 706 mounted on lead bodies 701. In these embodiments, the retention feature 706 comprises a sleeve 730 having at least one fanned end. The sleeve 730 may be comprised of a metal (e.g. nitinol) or polymer (e.g. polyimide) and extends around the lead body 701. The fanned end includes a plurality of projections 732 which are capable of fanning or extending radially outwardly from the lead body 701. In some embodiments, the sleeve 730 is slit or sliced to form the projections 732 of the fanned end. The sleeve 730 may be affixed to the lead body 701 or advanceable along the lead body 701 to adjust its position. During delivery, the fanned ends are covered by a sheath, delivery catheter or other suitable device. The lead 700 is advanced to a desired position and the sheath is withdrawn allowing the projections 732 to extend radially outwardly. FIG. 11A illustrates a sleeve 730 having one fanned end to resist movement in one direction. FIG. 11B illustrates a sleeve 730 having two fanned ends, each facing opposite directions so as to resist movement in both directions. FIG. 11C illustrates a plurality of sleeves 730, each having a single fanned end, so as to anchor the lead body 701 at various locations. It may be appreciated that a variety of combinations may be used.

Figure 12:
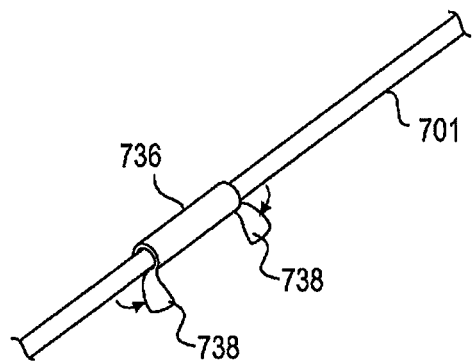
FIG. 12 illustrates a retention feature comprising a sleeve having at least one protrudable end.

FIG. 12 illustrates another embodiment of a retention feature 706 of the present invention. In this embodiment, the retention feature 706 comprises a sleeve 736 having at least one protrudable end. The sleeve 736 may be comprised of a metal (e.g. nitinol) or polymer (e.g. polyimide) and extends around the lead body 701. The protrudable end includes at least one projection 738 which is capable of extending radially outwardly from the lead body 701. In some embodiments, the sleeve 736 is cut to form the projections 738. The sleeve 736 may be affixed to the lead body 701 or advanceable along the lead body 701 to adjust its position. During delivery, the protrudable ends are covered by a sheath, delivery catheter or other suitable device. The lead 700 is advanced to a desired position and the sheath is withdrawn allowing the projections 738 to extend radially outwardly. FIG. 12 illustrates a sleeve 736 having two protrudable ends, each facing opposite directions so as to resist movement in both directions.

Figure 13:
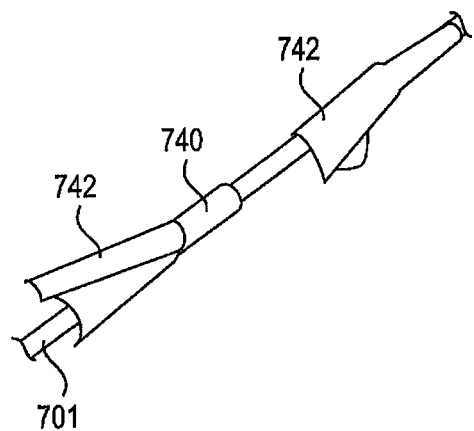
FIG. 13 illustrates a retention feature comprising a sleeve having at least one floppy end.

FIG. 13 illustrates another embodiment of a retention feature 706 of the present invention. In this embodiment, the retention feature 706 comprises a sleeve 740 having at least one floppy end. In this embodiment, the sleeve 740 is comprised of a flexible polymer, such as ePTFE. The sleeve 740 is cut or sliced to form elongate strips 742. The sleeve 740 may be affixed to the lead body 701 or advanceable along the lead body 701 to adjust its position. During delivery, the floppy ends may be covered by a sheath, delivery catheter or other suitable device to reduce drag by the floppy end during advancement. The lead 700 is advanced to a desired position and the sheath is withdrawn allowing the strips 742 to be revealed. The floppy ends provide resistance to movement of the lead body 701 in relation to the surrounding tissue. FIG. 12 illustrates two sleeves 740, each having one floppy end facing the same direction so as to resist movement in one direction.

Figure 14:
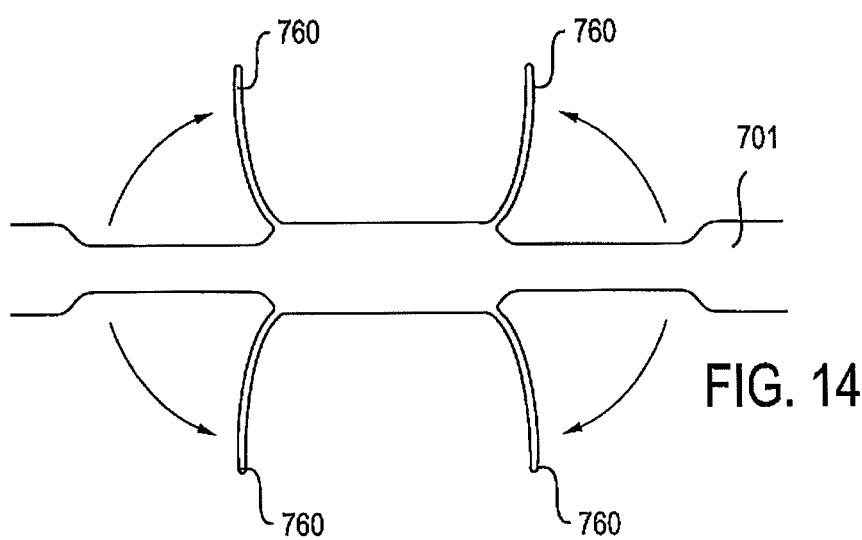
FIG. 14 illustrates a retention feature having one or more spring loaded projections.

FIG. 14 illustrates an additional embodiment of a retention feature 706 of the present invention. In this embodiment, the retention feature 706 comprises one or more spring loaded projections 760 which are extendable radially outwardly from the lead body 701 as shown. The projections 760 may be cut from the lead body 701, molded in or to the lead body 701 or attached via a secondary process. Optionally, the projections 760 may reside within pockets, indents or windows so as to minimize the profile of the lead body 701. The projections 760 may be comprised of the same or different material as the lead body 701. Example projection 760 material includes nitinol, or other metal, or preformed polymer. The projections 760 have a pre-set curved shape, such as a semi-circular shape, so as to curve radially outwardly from the lead body 701. Such curvature may be set by, for example, heating or tempering. Prior to deployment, the pre-formed projections 760 may be held along the lead body 701 by an external sheath or delivery device. Retraction of the sheath or delivery device exposes the pre-formed projections 760 allowing the projections 760 to recoil radially outwardly. Thus, the projections 760 extend into the surrounding tissue, resisting movement of the lead body 701 in relation to the tissue thereby anchoring the lead 700. The projections 760 may have any suitable size, shape and dimension, including a flat strip or elongate shaft. The tips of the projections 760 may be blunt or sharpened, or have other shapes, such as barbed or fish-hooked. The projections 760 may extend at any angle or a plurality of angles from the lead body 701 so as to resist movement in a variety of directions.

Figure 15A:
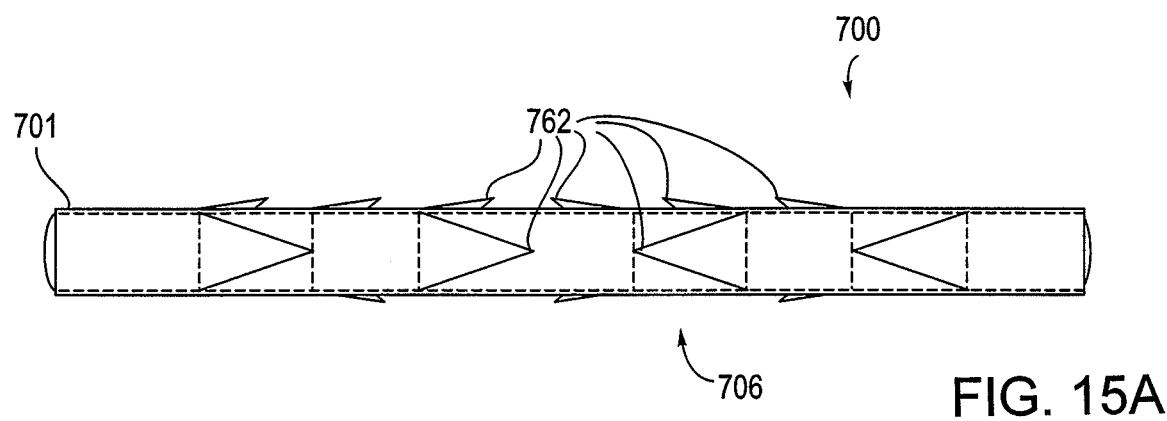
FIGS. 15A-15B illustrate a retention feature having a plurality of projections.
Figure 15B:
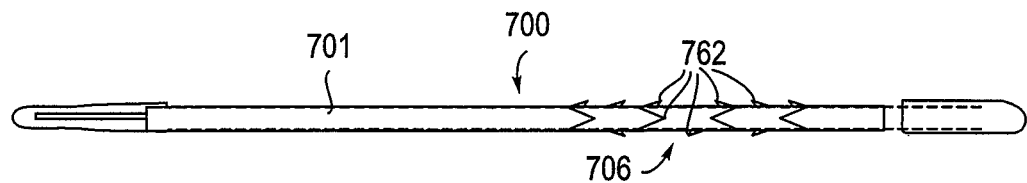

FIGS. 15A-15B illustrate another embodiment of a retention feature 706 mounted on a lead body 701. In this embodiment, the retention feature 706 comprises a plurality of projections 762 extending along the lead body 701. The projections 762 each have a pointed or triangular shape, however it may be appreciated that the projections 762 may have any suitable shape. The projections 762 may be formed from a flexible material, such as ePTFE or polyurethane, or a more rigid material, such as nylon. The projections 762 are aligned in rows, each row circumscribing the lead body 701. The rows are spaced apart along a portion of the lead body 701 so as to create a larger retaining surface. During delivery, the projections 762 may be covered by a sheath, delivery catheter or other suitable device. The lead 700 is advanced to a desired position and the sheath is withdrawn allowing the projections 762 to be revealed. The projections 762 provide resistance to movement of the lead body 701 in relation to the surrounding tissue. When the projections 762 are formed from flexible material, the projections 762 provide drag. When the projections 762 are formed from a more rigid material, the projections 762 may penetrate into surrounding tissue to anchor the leady body 701 during relative motion. FIG. 15A illustrates projections 762 facing two directions so as to resist movement in two directions.

Figure 16A:
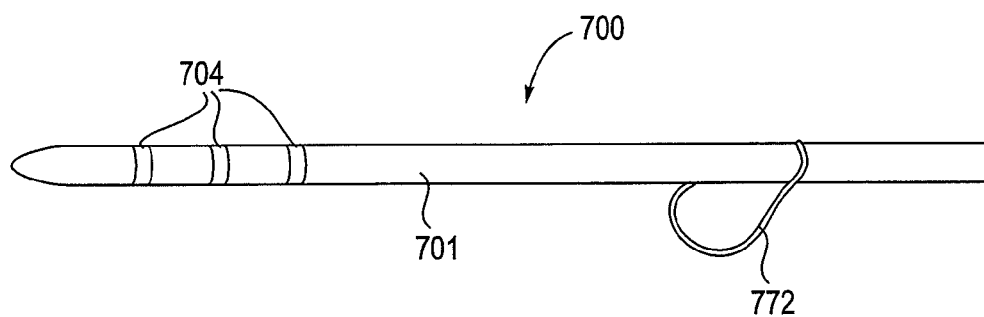
FIGS. 16A-16C illustrate a retention feature having a loop shape.
Figure 16B:
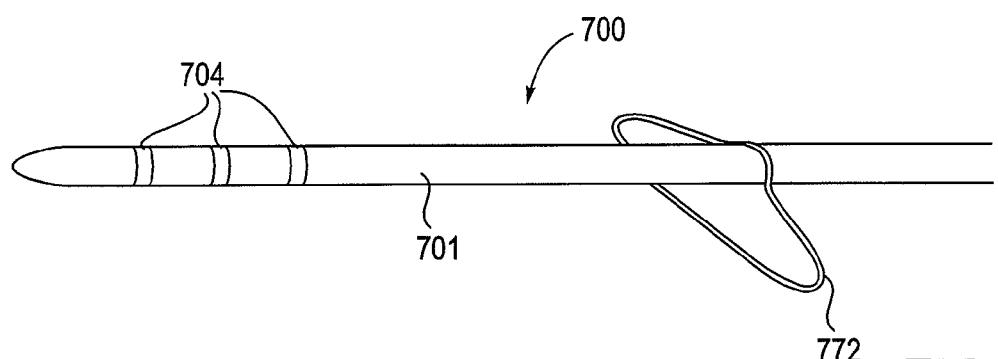
Figure 16C:
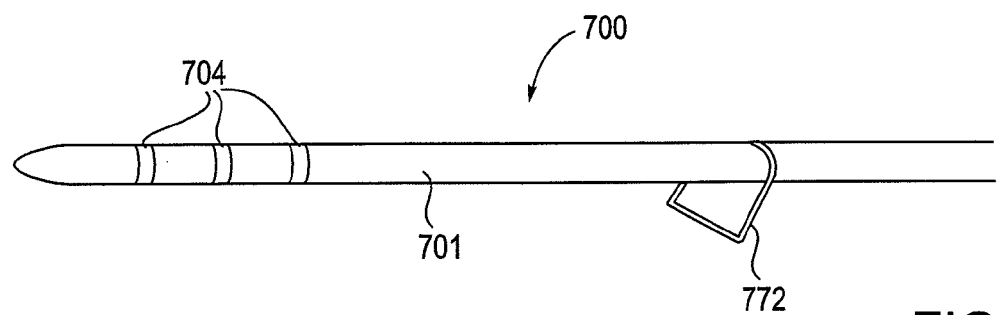

FIGS. 16A-16C illustrate a similar embodiment of a retention feature 706. Here, rather than a coil shape, the retention feature 706 forms a loop 772 which extends outwardly from the lead body 701. The loop 772 provides resistance to movement of the lead body 701 in relation to the surrounding tissue, such as by providing friction. The loop 772 may have a circular, oval, oblong, irregular, pointed, curved, square, rectangular or other shape.

Figure 17A:
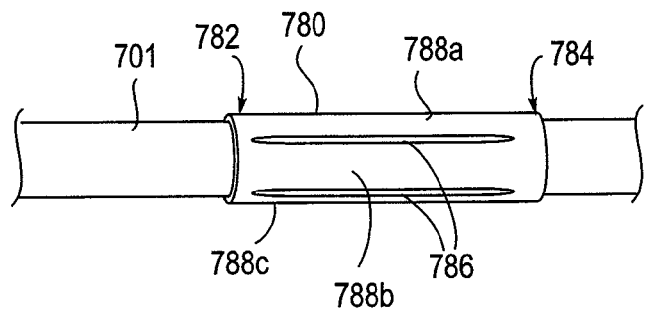
FIGS. 17A-17B illustrate a retention feature comprising a tubular structure having extendable struts.
Figure 17B:
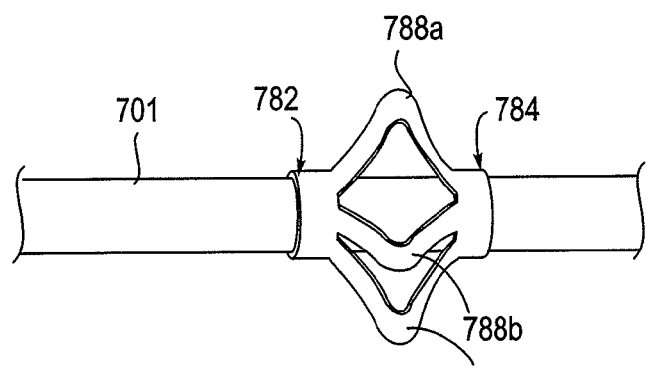

FIGS. 17A-17B illustrate an embodiment of a retention feature 706 comprising a tubular structure 780 having a first end 782, a second end 784 and longitudinal slits 786 therebetween along its length forming struts 788a, 788b, 788c (additional struts may be present though not illustrated). The tubular structure 780 is positionable over the lead body 701 and can be optionally advanced along the lead body 701 for desired placement. FIG. 17A illustrates the retention feature 706 in an arrangement suitable for such delivery. Once the lead body 701 is desirably placed, the retention feature 706 is actuated. Such actuation involves pushing the ends 782, 784 towards each other so that the structure 780 buckles and the struts 788a, 788b, 788c protrude radially outwardly, as illustrated in FIG. 17B. The projecting struts provide resistance to movement of the lead body 701 in relation to the surrounding tissue, thereby anchoring the lead body 701 in place. To reposition the lead body 701 and/or the retention feature 706, the ends 784, 786 may be drawn apart to retract the struts and then later pushed together again for anchoring. In addition, the slits 786 may allow tissue ingrowth over time to further anchor the lead body 701.

Figure 18A:
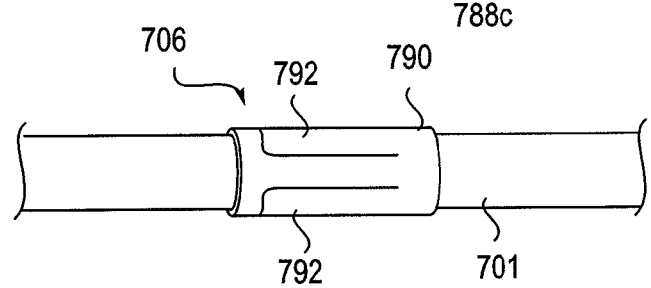
FIGS. 18A-18B, 19, 20 illustrate a retention feature having at least one extendable flap.
Figure 18B:
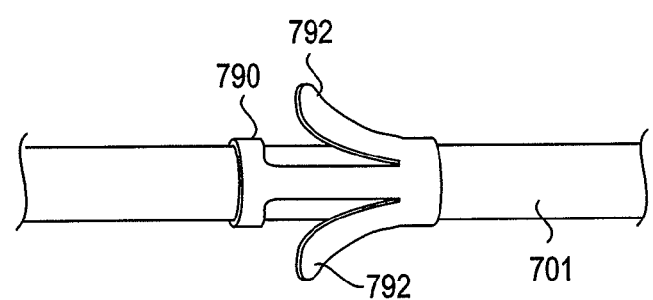

FIGS. 18A-18B illustrate an embodiment of a retention feature 706 comprising a tubular structure 790 having at least one extendable flap 792. The tubular structure 790 is positionable over the lead body 701 and can be optionally advanced along the lead body 701 for desired placement. FIG. 18A illustrates the retention feature 706 in an arrangement suitable for such delivery. During delivery, the retention feature 706 is covered by a sheath, delivery catheter or other suitable device. The lead 700 is advanced to a desired position and the sheath is withdrawn allowing the extendable flaps 792 to extend radially outwardly. The extendable flap 792 may be comprised of a pre-shaped polymer or shape-memory metal, to name a few. The projecting flaps 792 provide resistance to movement of the lead body 701 in relation to the surrounding tissue, thereby anchoring the lead body 701 in place.

Figure 19:
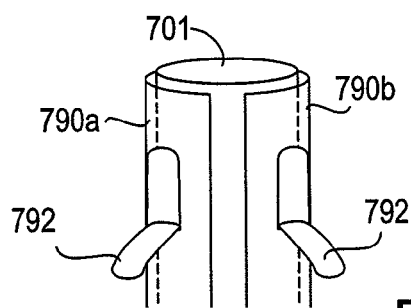
Figure 20:
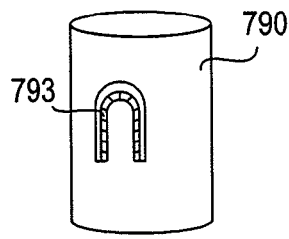

FIG. 19 illustrates an embodiment of a retention feature 706 similar to the retention feature 706 illustrated in FIGS. 18A-18B. In this embodiment, the tubular structure is split into two half-tubes or arc-shaped sheaths 790a, 790b which are positionable over the lead body 701. This is particularly suitable for flat or oval shaped leads wherein the arc-shaped sheaths 790a, 790b would have a greater ability to clamp on. The arc-shaped sheaths 790a, 790b may be independently advanced or retracted. Likewise, a single arch-shaped sheath may be used. It may be appreciated that the extendable flaps 792 may also include reinforcing material 793, as illustrated in FIG. 20. Such reinforcing material 793 may provide additional strength for anchoring purposes. Or, the reinforcing material 793 may provide the shape-memory feature wherein the remainder of the tubular structure 790 and flap 792 are comprised of a non-shape memory material.

Figure 21A:
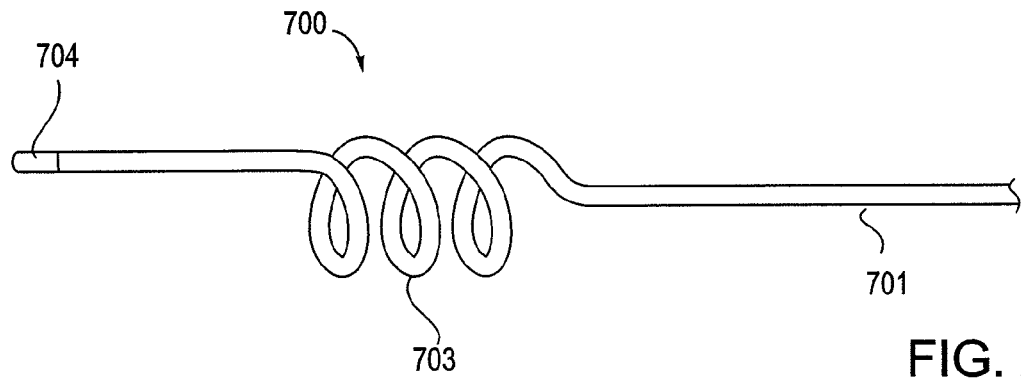
FIGS. 21A-21B, 22A-22B illustrate a retention feature built into a lead body.
Figure 21B:
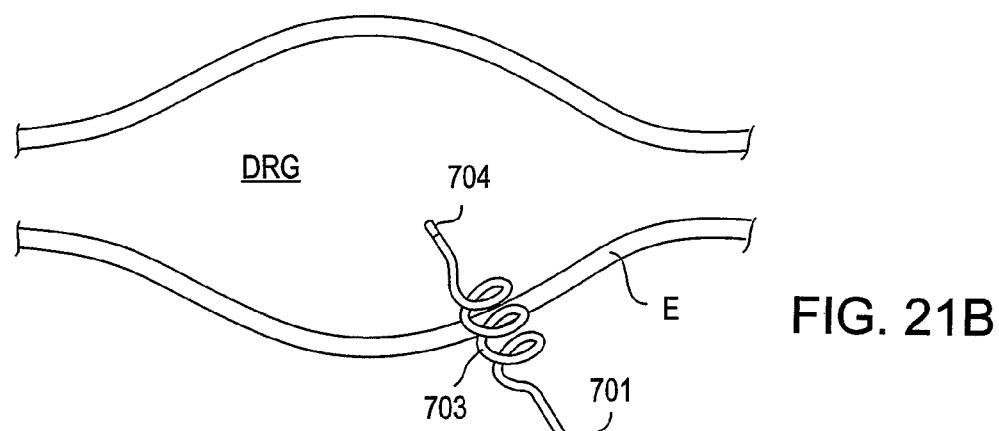
Figure 22A:
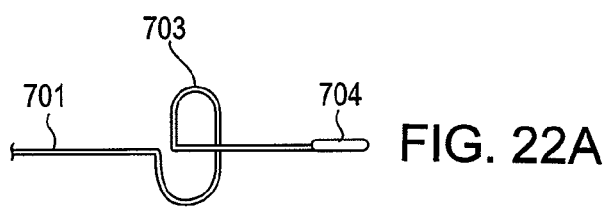
Figure 22B:
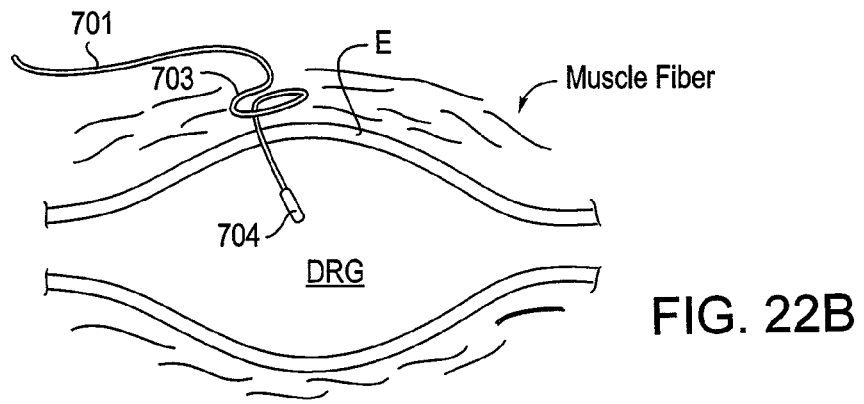

In some embodiments, the retention feature 706 is built into the lead body 701 itself. For example, FIGS. 21A-21B illustrate an embodiment of a lead 700 having lead body 701 of which a portion is shaped to provide retention or anchoring. As shown, the retention portion of the lead body 701 has a coil shape 703. The coil shape 703 assists in anchoring the lead body 701 to the surrounding tissue. FIG. 21B illustrates the lead 700 having an electrode 704 positioned so that the electrode 704 is implanted within the DRG. In this example, the coil shape 703 crosses the epinurium E of the DRG, holding the lead 700 in place. In addition, the coil shape 703 may provide strain relief for the lead 700. FIGS. 22A-22B illustrate a similar embodiment. Here, the coil shape 703 is disposed within tissue outside of the DRG while the electrode 704 is implanted within the DRG. It may be appreciated that the coil shape 703 may alternatively be disposed within the DRG for anchoring or retention.

Conventional fixation means generally require some solid or semi solid tissue in which to embed. In contrast, some implantation sites—such as the space surrounding the DRG—may be semi-fluid or lack solid tissue to provide a secure fixation field. Moreover, the space surrounding the DRG is quite variable and unpredictable, making many conventional fixation means unreliable and challenging. The retention feature embodiments of FIGS. 23A, 23B, 24A and 24B are designed to overcome these challenges and provides suitable lead retention capabilities in a variety of anatomical situations.

Figure 23A:
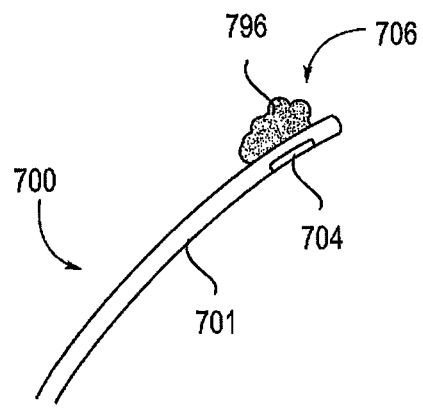
FIGS. 23A and 23B illustrate a retention feature comprising an expandable material.
Figure 23B:
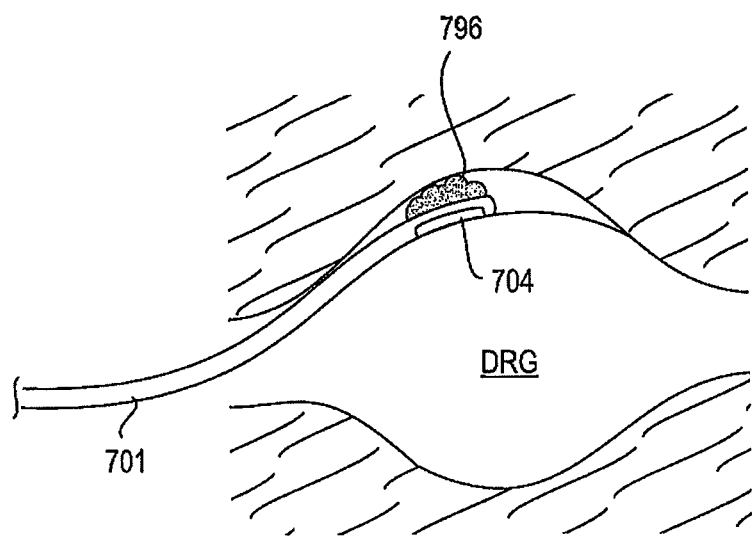

FIGS. 23A-23B illustrate another embodiment of a retention feature 706 of the present invention. In this embodiment, the retention feature 706 assists in holding the lead 700, particularly one or more electrodes 704, against a desired portion of the anatomy, such as the dorsal root ganglion DRG. FIG. 23A illustrates the lead 700 having an expandable material 796 mounted on a portion of the lead body 701, particularly along a portion of the lead body 701 opposite or near to the one or more electrodes 704. The expandable material 796 may be comprised of a sponge, SuperPorous HydroGel or other swellable or expandable material. It may also be appreciated that an expandable mechanism, such as a balloon, may alternatively be used. FIG. 23B illustrates the lead 700 positioned within the spinal anatomy so that the one or more electrodes 704 are desirably positioned near the target anatomy (in this example, the DRG). The expandable material 796 is then expanded, thereby wedging the lead body 700 between the DRG and the surrounding tissue or muscle. The supportive force of the tissue holds the one or more electrodes 704 against the DRG which assists in retention of the lead 700 in the desired position.

Figures 24A, 24B:
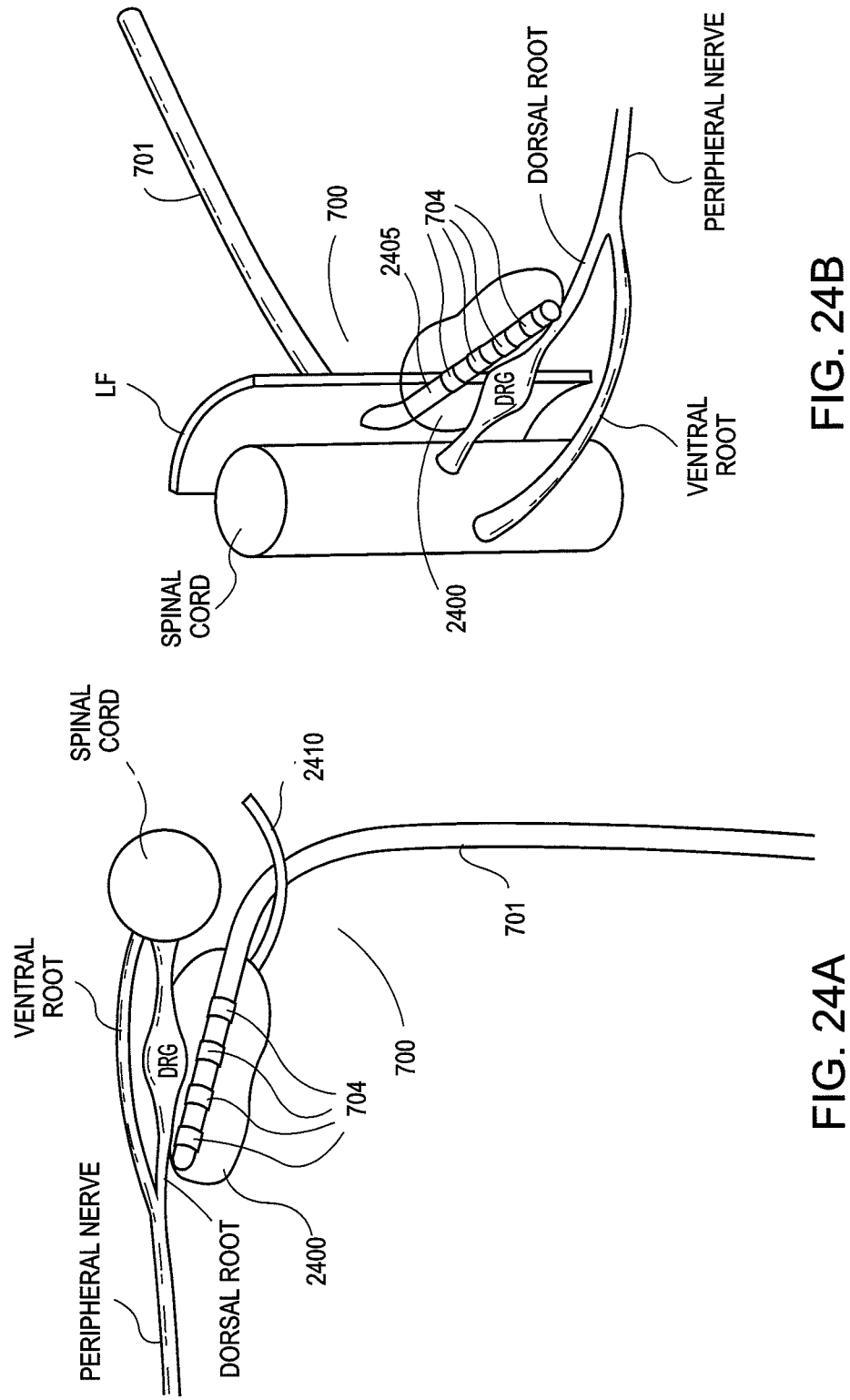
FIGS. 24A and 24B illustrate the use of a injectable gel or expandable medium as a retention feature.

In other embodiments, a medium is injected near the target anatomy rather mounted on a portion of the lead body. FIGS. 24A and 24B illustrate perspective views of a lead held in position using an injectable medium. In these examples, an injectable gel or other injectable medium 2400 is introduced into the volume surrounding the lead body, lead tip, electrodes and/or targeted neural tissue. The injectable medium may optionally be an expandable medium wherein it expands upon delivery. The injectable gel or other injectable medium 2400 is injected such that, immediately or when expanded, it completely or partially fills the space around the lead and targeted neural tissue. The medium 2400 will reduce the amount of relative motion between the distal lead and the targeted neural tissue, thus helping to reduce any migration of the lead or possible change in efficacy of the therapy. The injectable nature of the medium allows any desired quantity of medium to be injected, including large quantities, without increasing the size of the lead. This maintains ease of lead implantation regardless of the size of the anatomical void to be filled.

The medium 2400 can be introduced in a number of ways. For example:

(a) through an introducing needle before the lead is inserted, as long as the medium 2400 is designed to allow proper placement of the lead;

(b) through a central lumen in the lead and/or through a port 2405 (FIG. 24B);

(c) through an introducing needle 2410 after the lead has been placed (FIG. 24A).

The medium 2400 may be comprised of various types of biocompatible compounds such as PLGA, microspheres, hydrogel and the like. The medium 2400 can be biodegradable or not, depending on clinical requirements. In addition, the medium 2400 can contain radiopaque compounds to help visualize its extent under fluoroscopy. Also, the medium 2400 can contain an anti-inflammatory compound such as Dexamethasone, or other therapeutic agent, which can be encapsulated for time release if desired. As discussed elsewhere, the anti-inflammatory agent could reduce scarring and help maintain low impedance between electrodes and nearby nerve tissue, thereby reducing energy consumption of the stimulation system.

This lead retention technique has numerous advantages over conventional fixation techniques and devices. The amount of medium 2400 and the location of the insertion can be varied to accommodate varying anatomy in the vicinity of a targeted neural side or neural tissue. The medium can be biodegradable so that the subsequent scarring around the electrodes can fix the lead in place. In addition, if the lead needs be removed, the medium can remain behind and simply dissolve or be absorbed. The medium 2400 is soft and conforming to surrounding tissue so that potential damage to nearby tissues is reduced. Also, discomfort and potential tissue damage due to flexation of the patient is reduced. In addition, the lead can be easily removed without tissue damage.

The medium 2400 can contain time released or immediately active anti-inflammatory agents or other therapeutic agents. The medium 2400 can contain a radiopaque substance for visualization. The medium 2400 may also be introduced in sufficient volume that the medium encapsulates both the electrodes and the targeted neural tissue. In the DRG example, sufficient medium would be introduced to encapsulate the one or more electrodes in the area around the DRG and all or a portion of the DRG or dorsal root. Optionally, the properties of the medium 2400 may be chosen to enhance or mitigate transmission of stimulation energy from the one or more electrodes.

The various embodiments described in FIGS. 23A, 23B, 24A, and 24B describe a system including a lead having a lead body and at least one electrode; and a retention feature disposed along the lead body proximal to the at least one electrode and configured to assist in atraumatically anchoring the lead to nearby tissue when the lead is positioned in the body. In one aspect, the retention feature comprises a medium. In another aspect, the retention feature in the form of a medium is injected into a volume near or including a portion of the electrode or the targeted neural tissue. In still another variation, there is a port in the electrode body adapted and configured for injecting the medium.

Figure 25:
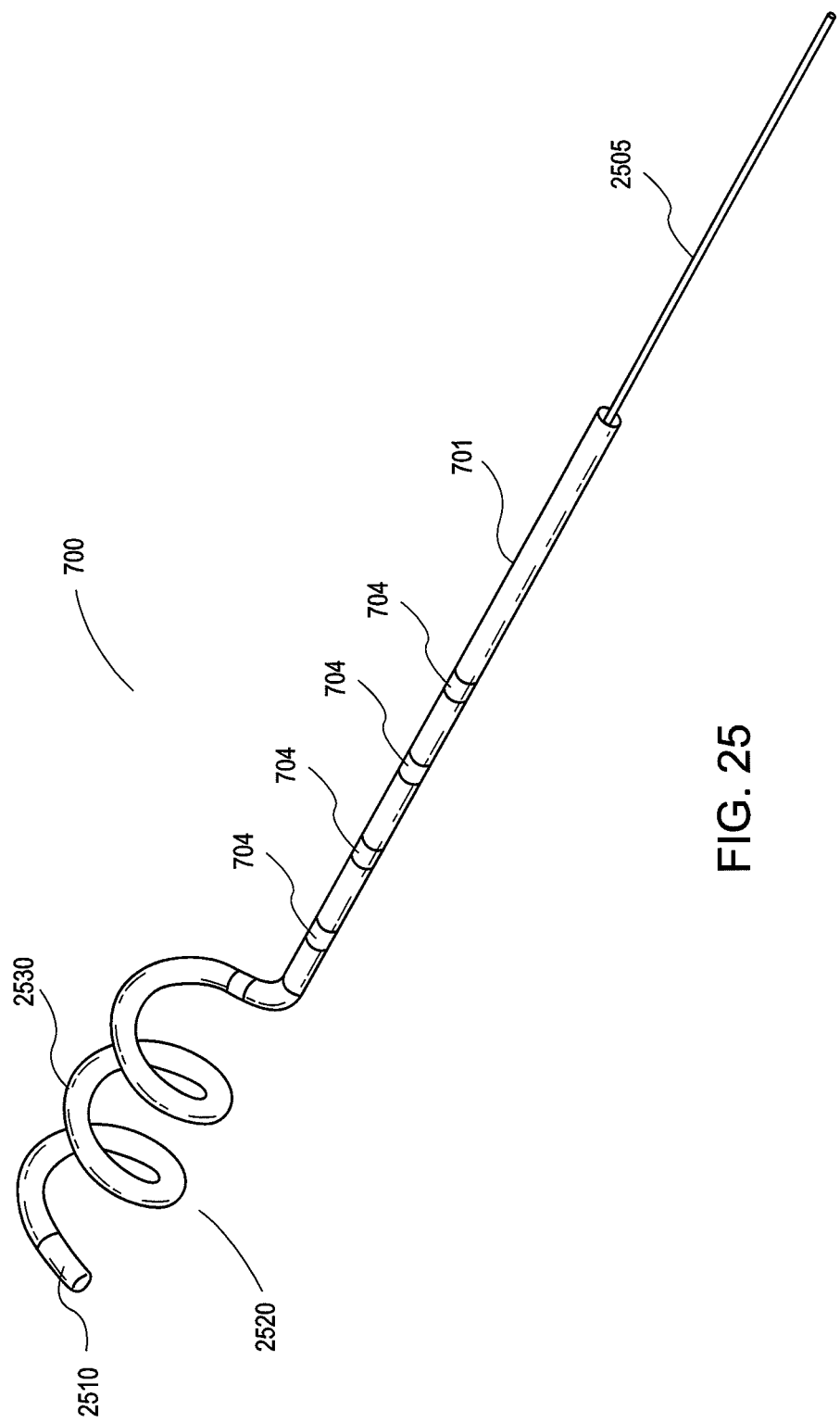
FIG. 25 illustrates a perspective view of any stimulation lead having a controllably deformable tip.

In other embodiments, the stimulation lead 700 includes a controllably deformable section which may act as a retention feature. FIG. 25 illustrates a perspective view of an embodiment of a stimulation lead 700 having a controllably deformable section 2520. The stimulation lead 700 includes a lead body 701 and the number of electrodes 704. An actuation cable 2505 extends through the lead body 701 and the controllably deformable section 2520 and is attached to tip 2510. Manipulation of the actuation cable 2505 causes deformation of the controllably deformable section 2520. The controlled deformation of section 2520 may produce predictable, temporary curved movements of the section 2520 that are used for steering. A shape conductive to steering may include, for example, a simple curve of the controllably deformable section 2520 near tip 2510. These movements allow a user to steer the lead tip 2510 during a lead implant procedure through manipulation of the actuation cable 2505. Once the lead is in a desired position for implantation, the actuation cable 2505 is manipulated again in order to deform the deformable section 2520 into a shape adapted and configured for retaining the position of the lead.

Embodiments of stimulation lead 700 having a controllably deformable section 2520 have a number of advantages over conventional stimulation leads. This innovative lead design employs a controllably deformable section geometry to post-operatively retain the lead in a desired location and or allow a user to steer or manipulate the lead during a lead placement process. The actuation cable 2505 may be manipulated directly by the user or by an actuation mechanism to provide the desired deformation and/or steering function. A suitable actuation mechanism would include a handle and would attach the actuation cable 2505 to a suitable lever, switch, or grip that, when operated, produces the appropriate movement of the actuation cable 2505 to produce the desired steering and/or deformation of the deformable section 2520.

Conventional lead placement typically involves surgically invasive implantation procedures, lead movement techniques that cannot be localized to the lead tip or to selected portions of the lead relative to the electrode(s), are often limited to only a single actuation or become difficult to remove once implanted. Embodiments of stimulation lead 700 do not have these limitations. Advantageously, leads having a controllably deformable section 2520 allow easy, non-invasive, reversible, repeatable actuation of the controllably deformable section 2520. Additionally, the placement of the deformable section 2520 along the lead body 701 and/or relative to an electrode 704 may be selected so that the lead placement conforms to the anatomy at a targeted stimulation site or tissue location. Another advantage is that the design of the controllably deformable section 2520 does not add to the overall lead body diameter and does not therefore require a larger gauge introducing needle. Because the design provides for steering of the lead, the number and overall diameter of components needed to position and retain the lead is reduced. As a result of the design of and cooperation between the controllably deformable section 2520 and the actuation cable 2505, it is believed that the embodiments of the lead having a controllably conformable section 2520 may be steered and implanted without the use of a steerable stylet, guide catheter, guide wire, or other conventional steering or implant aid used by conventional stimulation leads.

The embodiment illustrated in FIG. 25 shows the controllably deformable section 2520 in a deformed condition to promote lead retention. In the illustrated deformed condition, the section 2520 forms a number of coils 2530. Various other geometries of the controllably deformable section 2520 may also be effective in lead retention, such as, for example, curling the controllably deformable section 2520 in one or more planes, or any other deformation that increases the overall aspect ratio of the controllably deformable section 2520 in order to inhibit the lead 700 from moving out of position. Accordingly, the controllably deformable section 2520 may assume any of a number of two-dimensional, three-dimensional or complex shapes in order to promote lead retention. Alternatively, the controllably deformable section 2520 may, when deformed for lead retention purposes, assume the shape of any lead retention feature described herein.

The actuation cable 2505 extends through the lead body 701, such as through an internal lumen, and is a fixed to the distal end of the lead 700, such as at tip 2510. Actuation of the controllably deformable section 2520 for steering or lead retention is accomplished, for example, when a user holds the proximal end of the lead body 701 stationary while the actuation cable 2505 is moved axially. As such, actuation can occur either by pulling the end of the actuation cable or, alternatively, by releasing it, depending upon the design of the actuator. It is to be appreciated that actuation of the actuation cable 2505 and the movement of the controllably deformable section 2520 may be performed multiple times, may be reversibly performed, alternate between steering and retention or any other such combination of movements as desired by the user until the actuation cable 2505 is secured in a final position. Moreover, manipulation of the actuation cable 2505 and controlled deformation of the controllably deformable section 2520 may also be used to free the lead 700 from the implant site should the lead 700 ever need to be removed.

In some embodiments, the proximal portion of the lead body 701 is stiffened to enhance the operation of the actuation cable 2505. When present, this stiffer lead body portion may also allow torque transmission from proximal to distal portions of the lead that would enhance the steering capabilities of the distal tip 2510. The distal portion of the lead will be adequately flexible such that manipulation of the actuation cable 2505 produces the desired steering and/or deformation.

The actuation cable 2505 may perform several functions. The actuation cable 2505 may provide axial strength to the lead body 701, as an electrical lead to provide stimulation energy to the electrodes at 704 or as a steering device as described above. While a single controllably deformable section 2520 and a single actuation cable 2505 are illustrated in FIG. 25, this aspect of the present invention is not so limited. In some embodiments, more than one actuation cable 2505 or controllably deformable section 2520 may be used. The controllably deformable section 2520 may form retention shapes other than the coils 2530 illustrated. The controllably deformable section 2520 may be positioned at other locations other than distal to the electrodes 704, such as proximal to the electrodes. One or more controllably deformable sections 2520 may be positioned distal to the electrodes 704, proximal to the electrodes 704, partially or completely overlapping one or more electrodes 704 or positioned in any combination thereof.

The materials used in the formation of the lead 700 illustrated in FIG. 25 are selected to be biocompatible and suitable for long-term implantation in the body. The lead body 701 may be formed from polymers of various materials, durometers, profiles, and construction, such as Tecoflex, Pellathane and other polymer family members and/or composite polymer structures such as an overmolded polyamide. The controllable distal section 2520 can include radio opaque markers or materials to indicate under fluoroscopy actuation or position of the tip 2510 or a portion (such as an end of or middle) of the deformable section 2520. The tip 2510 may also contain radiopaque materials. The tip 2520 and the deformable section 2520 may include materials such as cobalt-chrome, platinum alloys, stain steel, titanium, nitinol and combinations thereof. Alternatively, the tip 2510 is formed from any of the polymers described herein or within the knowledge of those of ordinary skill in the art. The actuation cable 2505 may be a single strand or a multiple strand structure or a braided structure having strands or braids formed from a metal, a metallic composite, a polymer, a polymer composite or any combination of the above.

FIGS. 26A-26C illustrate various views of an embodiment of a lead 700 having a lead retention feature 2603 embedded into a controllably deformable section 2600. When retaining the position of the lead, the lead retention feature 2603 has a deformed, non-straight configuration as shown in FIG. 26B. As used herein, the deformed configuration of the lead retention feature 2603 includes any hook, loop, curve, band, coil, two-dimensional shape, three-dimensional shape or any retention feature shape described herein. Typically, a lumen 2610 extends through and within the lead body 701. The retention feature 2603 extends alongside the lumen 2610 and is embedded into or affixed to the lumen wall. The lumen 2610 is sized to receive a stylet 90.

FIG. 26A illustrates a section view of the lead 700 with the stylet 90 inserted into the lumen 2610. In this configuration, the stylet 90 maintains the controllably deformable tip 2600 in a straight or unbend configuration as illustrated in FIG. 26A for delivery. This configuration simplifies placement and manipulation of the lead 700 during an implantation procedure.

FIG. 26B illustrates a section view of the lead 700 resulting from proximal retraction of the stylet 90. With the counterbalancing force provided by the stylet 90 removed from the controllably deformable section 2600, the lead retention feature 2603 moves into its deformed configuration and produces a corresponding deformation of the controllably deformable section 2600. The resulting shape of the controllably deformable section 2600 is any shape suited to aid in retaining the lead 700 in position or to prevent or minimize migration of the lead 700. For example, the resulting shape of the controllably deformable section 2600 may be any of the lead retention shape described herein.

FIG. 26C illustrates a perspective view of the lead 700 with the stylet 90 removed. Thus, the controllably deformable section 2600 is shown in a deformed or lead retention configuration.

An exemplary implantation procedure for the lead 700 will be described with reference to FIGS. 26A-26C. To percutaneously insert the lead 700 through an introducing needle, the lead 700 is first straightened by introducing a relatively stiff stylet 90 into the proximal end of the lead into a lead lumen 2610 and advanced to the distal end as shown in FIG. 26A. The stylet 90 forces the lead 700 and retention element 2603 to straighten as shown in FIG. 26A. The stylet 90 remains in place in the lead 700 until the lead 700 is deemed to be in the desired therapeutic location. Next, as shown in FIG. 26B, the stylet 90 can be removed by withdrawing it proximally. This action frees the retention feature 2603 so that it deforms or reshapes the controllably deformable section 2600. The shape of the controllably deformable section 2600 is then used to hold the lead 700 in place. Actuation of the retention feature 2603 can be performed multiple times and reversed, as desired.

Several advantages of this embodiment will be described. The embodiments illustrated in FIGS. 26A-26C provide a simple, noninvasive, reversible, repeatable actuation of the distal lead tip simply by withdrawing the stylet 90. Actuation of the controllably deformable section 2600 occurs automatically when removing the stylet 90 thereby adding no further complications to the surgical procedure. The shape of the controllably deformable section 2600, when deformed may conform to the anatomy, which has the advantage of reducing potential irritation or damage to the nearby tissue. The controllably deformable section 2600 design does not add to the overall lead diameter, and does not require a larger introducing needle gauge. If Nitinol or other metal is used to form the retaining element 2603 it may be possible to image the element 2603 under fluoroscopy to help ensure proper deployment and lead position.

Another embodiment of a lead 700 having a lead retention feature is illustrated in FIGS. 27A-27B, 28A-28B, 29A-29B, 30. In this embodiment, the lead 700 includes a lead body 701 attached to a lead tip 2700 and a lead retention feature 2703 stowed within the lead tip 2700. In contrast to the lead retention feature 2603 described above, the lead retention feature 2703 of this embodiment is movable relative to the lead tip 2700. The position of a stimulation lead after implantation is achieved via the intra-operative actuation of the lead retention feature 2703 stowed within the lead tip 2700. When deployed from the lead tip 2700, the retention feature 2703 increases the geometric aspect ratio of the lead and may inhibit undesired post operative migration of the lead and the stimulation electrodes. While illustrated as a single retention feature 2703 exiting generally from the distal end of the lead and along the longitudinal axis of the lead body, it is to be appreciated that multiple retention features may be employed and that a retention feature may be stowed within and exit from portions of the lead other than the distal most portion of the tip and at angles, positions or orientations that are not aligned with the longitudinal axis of the lead body or at an angle relative to the longitudinal axis of the lead body.

In one embodiment, the retention feature 2703 is a long thin spring located in the relatively stiff lead tip 2700 positioned at the distal end of the flexible lead body tubing. This thin spring retention feature, when not otherwise constrained, has a non-straight geometry, such as, for example, a loop, a hook, one or a plurality of coils, or any two-dimensional shape, three-dimensional shape, complex shape or, alternatively the shape of any lead retention feature described herein.

The various details of the illustrated lead 700 will be described with reference to the various views shown in FIGS. 27A-29B. The lead tip 2700 has a distal end 2705 and a proximal end 2710. A proximal lumen 2722 extends from the proximal end 2710 to an inner ridge 2725 (FIG. 27B). As will be further described below and is shown in FIG. 27A, the proximal lumen 2722 is sized to receive either a stylet 90 or a pusher wire 95. The inner ridge 2725 is sized to prevent the passage of the stylet 90 into the distal lumen 2720. The distal lumen 2720 is coextensive with the proximal lumen 2722, extends from the inner ridge 2725 to the distal end 2705 and is sized to only receive a pusher wire 95 (i.e., distal lumen 2720 has a diameter smaller than the diameter of a stylet 90).

FIG. 30 illustrates a perspective view of a stimulation lead 700 having a lead tip 2700 as illustrated in the various section and enlarged views of FIGS. 27A-29B. FIG. 30 shows the stimulation leads 700 with the lead body 701 and electrodes 704 in place and with the retention feature 2703 extending beyond the lead tip distal end 2705. The lead body 701 joins the lead tip 2700 along the proximal end 2710. Appropriate sizing is found between the inner diameter of the lead body 701 interior and the outer diameter of the lead tip between the proximal end 2710 and an outer ridge 2715. Typically, the lead body 701 and the lead tip 2700 are joined using the area between the outer ridge 2715 and the lead tip the proximal end 2710.

For clarity, the lead body 701 is not illustrated attached to the lead tip 2700. The stylet 90 and the push wire 95 would pass through the lead body 701 before reaching the lead tip 2700. With the lead body 701 removed, the interactions between the stylet 90, the push wire 95, the retention feature 2703 and the lead tip 2700 are more readily appreciated.

FIGS. 28A-29B illustrate the cooperation between the retention element 2703 and the lead tip 2700. FIGS. 28A and 28B illustrate section views of the tip 2700 interior where the push wire 95 has advanced through the proximal lumen 2722, beyond the inner ridge 2725 and into contact with the lead retention feature proximal end 2706. (see FIG. 28B). FIG. 28A shows advancement of the push wire 95 to urge the retention feature 2703 beyond the distal end 2705. FIGS. 29A and 29B illustrate the continued advancement of the push wire 95 to further advance the retention feature 2703 beyond the lead to distal end 2705. In the illustrated embodiment of FIG. 29B the push wire 95 is used to advance the retention feature 2703 distantly within the lead 2700 until the shaped proximal end 2706 engages with the walls of the distal lumen 2720. The walls of the distal lumen 2720 and the exterior shape or surfaces of the retention feature proximal end 2706 have complementary shapes, features, protrusions, recesses or any other suitable mating surfaces to allow engagement between the walls of the distal lumen 2720 and the proximal end 2706.

The insertion of the lead 700 having a tip 2700 and retention feature 2703 will now be described with reference to FIGS. 27A-29B. The lead 700 is percutaneously introduced typically with a stylet 90 as shown in place within the lead tip 2700 (FIGS. 27A and 27B). The lead tip 2700 is formed such that the introducing stylet 90 does not push on the retention element 2703. When the lead 700 is deemed to be in the correct and final therapeutic location, the stylet 90 is removed. FIGS. 28A and 28B show a pusher wire 95 inserted into the lead 700 and advanced until it contacts and pushes on the retention element 2703. FIGS. 29A and 29B show the pusher wire 95 advanced until the retention element 2703 is fully extended. Typically, the retention feature proximal end 2706 will be locked in place within the distal lumen 2720 as shown in FIG. 29B. FIGS. 29A, 29B and 30 shows the retention feature 2703 assuming a curve or other deformed shape. The deformed shape of the retention feature 2703 serves at least two purposes. One purpose is to lock the retention element 2703 in place with respect to the lead and the lead tip. Another purpose is to hold the position of the lead distal end 2705 in place within the body near the stimulation site. In the illustrated embodiment, the proximal end 2706 and the lead tip lumen 2720 are formed such that the retention element 2703 does not extend completely beyond the distal end of the lead or completely exit the lead tip lumen 2720. If desired, the design can include features that allow multiple actuation so the retention element 2703.

The various embodiments illustrated and described in FIGS. 25-30 provide a system including a lead having a lead body and at least one electrode; and a retention feature disposed along the lead body proximal to the at least one electrode and configured to assist in atraumatically anchoring the lead to nearby tissue when the lead is positioned in the body. In some variations, the system includes a controllably deformable section. In some other variations, the retention feature is movable into a first configuration for steering the lead and a second configuration to act as a retention feature. In some specific variations, the retention feature is reversibly movable into the first and the second configurations. In still other variations, the retention feature is held into a non-bend configuration by a stylet and the retention feature moves into a retention configuration when the stylet is removed.

Figure 31A:
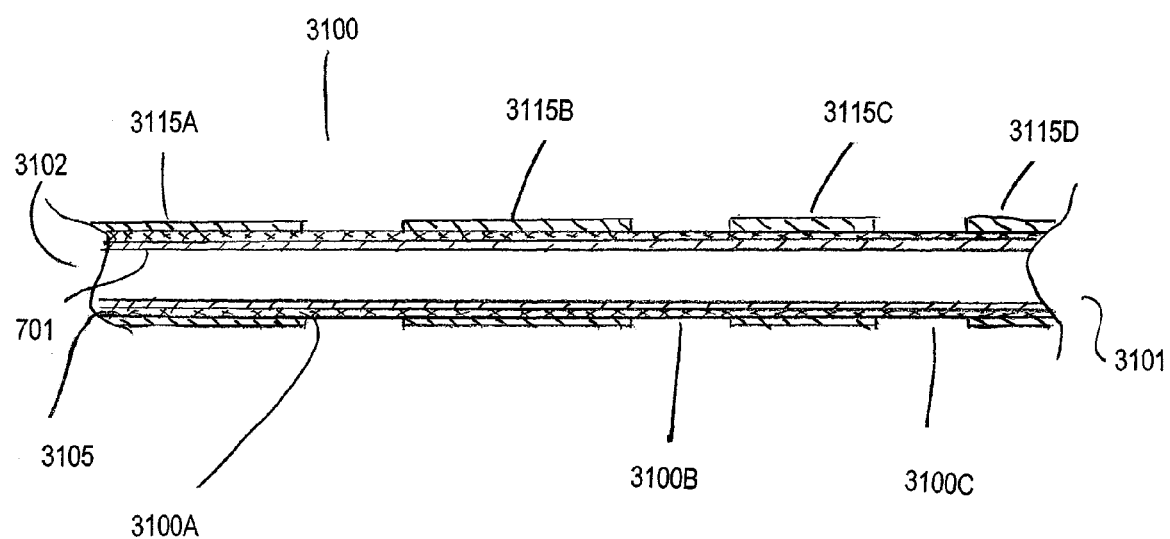
FIG. 31A illustrates a section view of a braided retention structure in a non-buckling configuration.
Figure 31B:
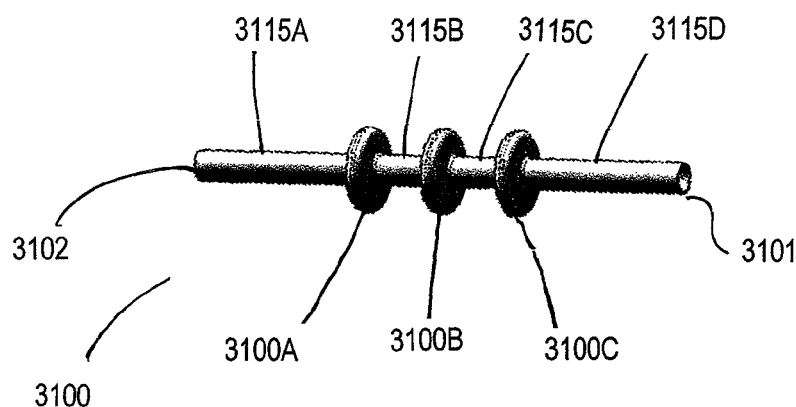
FIGS. 31B, 31C and 31D illustrate various braided retention structure embodiments in a buckled configuration.
Figure 31C:
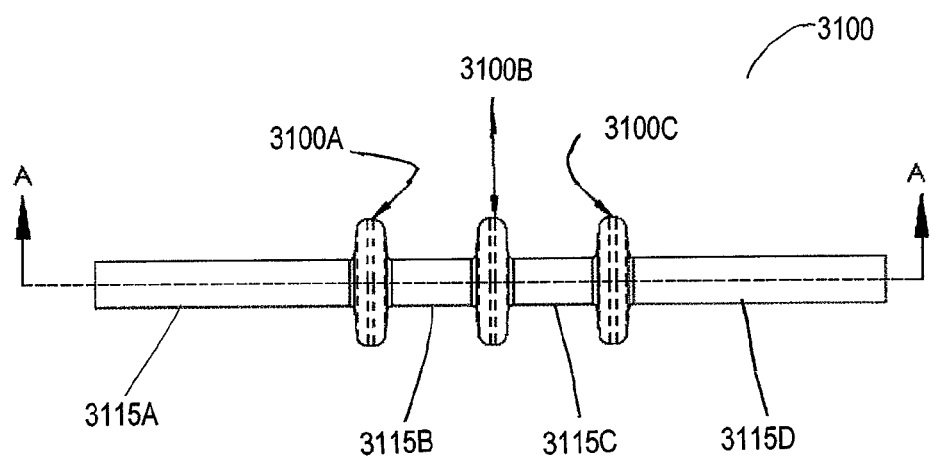
Figure 31D:
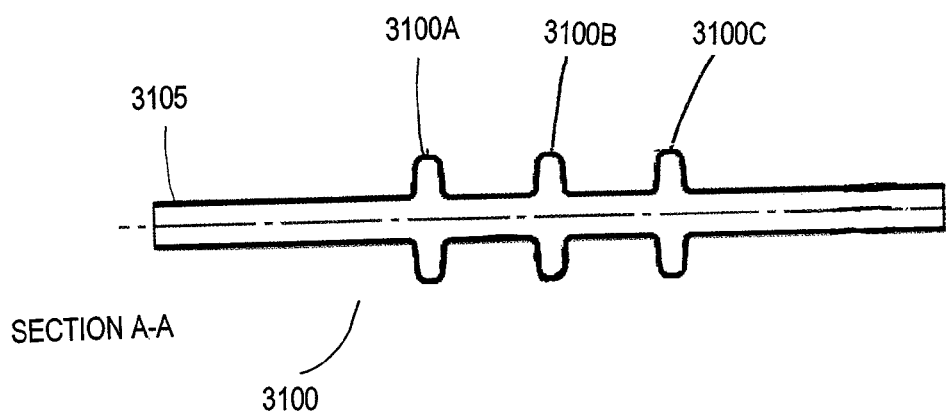

FIGS. 31A-31D illustrate another embodiment of a lead having a lead retention feature. In this embodiment, the lead retention feature comprises a braided retention section 3100. The braided retention section 3100 is designed with predefined buckling regions that when actuated will to form into braided retention features. As a result, the braided retention section 3100 is configurable from a straight configuration (FIG. 31A) to a buckled configuration as shown in FIGS. 31B, 31C and 31D. The braided retention section 3100 may be attached to the lead body 701 proximal to, distal to, partially overlapping or completely overlapping the portion of lead containing electrode 704.

The buckling regions on the braid can be created in a number of ways. For instance, the braid itself can be modified in areas that will buckle. The physical characteristics of the braid in these areas, such as, the braid fiber angle, density, number and/or diameter, are modified such that the modified area will preferentially buckle. Alternatively, the braid can remain unmodified but undergo treatment or conditioning such that certain areas will buckle. For instance, the non-buckling areas of the braid can be overlaid with a film or other strengthening agent. FIG. 31C illustrates reinforcing tubes 3115A-D performing such a function. Another means to create an area of buckling is to weaken the buckling areas by heating, truncating the fibers, or otherwise manipulating the braid so that a buckling mode is preferred in that area. Alternatively, the braid section may be formed by reinforcing areas of the braided structure so that buckling occurs in the non-reinforced regions of the braided structure.

One exemplary embodiment of this form of braided structure is illustrated in FIG. 31A. FIG. 31A is a section view of a braided structure 3105 placed over a lead body 701. Tubing reinforcements 3115A-D are placed along and reinforce portions of the braided structure 3105. As a result, unreinforced braided portions 3100A-D remain. When actuated, the distance between the tubing reinforcements 3115A-D decreases producing buckling or deformation of the unreinforced braided portions 3100A-D as shown in FIGS. 31B and 31C.

The braided retention section 3100 may be attached to or formed as part of the lead body 701 or, alternatively the braided retention section 3100 may be provided along the lead body 701 after the lead body has been implanted.

An exemplary implementation procedure may include the placement of the lead using a stylet and introducer needle. Once the lead is in place, the needle is removed and the stylet remains in place within the lead body. The braided fixation section 3100 is attached to a deployment tool or device used to slide the section 3100 along the lead body 701. The section

3100 diameter is selected to be slightly larger than the outer diameter of the lead body 701. The devices used to clamp, crimp or otherwise secure the section distal end 3101 to a desired position on the lead body 701. The position may be distal, proximal, partially overlapping or completely overlapping one or more of the electrodes 704 on the lead body 701. Next, the device is used to axially compress the section 3100 to produce a buckling or deformation (see FIGS. 31B, 31C and 31D). Thereafter, the device is used to clamp, crimp or otherwise secure the proximal end 3102 to the lead body 701. The buckled or deformed sections 3100A-3100C protrude from the lead body, and engage with surrounding tissue or structures in order to prevent or minimize migration of the lead 700.

In an alternative implementation and deployment scenario, the deployment tool is not used because the braided section 3100 is already attached to the lead body 701. The lead is positioned for applying stimulation. Next, an actuation rod or wire is attached to (or, alternatively, may already be attached to) the braided section 3100. Movement of the rod or wire produces the buckling/deformation shown in FIGS. 31B, 31C and 31D. Once buckled, the braided section 3100 is secured to the lead body using any suitable method.

This embodiment provides a number of advantages over conventional lead fixation. The braided retention section allows a simple, noninvasive, reversible, repeatable actuation of lead fixation when the lead is delivered to a targeted narrow side. The braided retention device does not require sutures or surgical procedures to maintain its position and it can be inserted or removed percutaneously with minimal impact to the patient. The braided retention device conforms to the anatomy, which has the advantage of reducing potential irritation and damaged to the nearby tissue. The braided structure contains no sharp features to injure the vasculature or adjacent nerves.

Variations and alternative configurations of the braided retention structure are possible. The braid or other components may be formed from a resorbable polymer material that may be used if the lead fixation is only required for a limited time. The polymer can be used for the lead body, the tube or the braid and may include radiopaque or other strands or markers to make the braided retention structure visible under fluoroscopy. The device components can be made out of metal such as nitinol, stainless steel and the like and may include the combination of a metal and a polymer. The deformed geometry of the braided retention structure may be offered in several different options, such as outer diameter and width of the buckled feature, distance between buckled features, stiffness of the braid and the like depending upon of different considerations. Varying types of braids can be used to maximize effectiveness of tissue in growth, the material selected for braid formation can promote tissue in growth or the braid may be coated with a material selected to promote tissue in-growth. Varying types of braids and materials can be used to reduce or increase the actuating force needed to induce buckling. The device can be fabricated such the tensile force is applied to change its geometry to a cylinder during insertion, or alternatively a compress the force is required to deform it. Actuation can be varied to change the amount of deformation thereby providing proportional buckling. Proportional buckling allows a user to control the buckling amount to agree that the user feels is appropriate under the circumstances. More than one braided section can be deployed on the lead body, for example, one distal and one proximal to the stimulation electrodes. The embodiments of FIGS. 31A-31D illustrate three similarly sized and shaped buckling sections 3100A-C. It is to be appreciated that more or fewer buckling sections may be used, that buckling sections may be of different relative sizes and different shapes.

The various embodiments illustrated and described in FIGS. 31A-31D provide a system including a lead having a lead body and at least one electrode; and a retention feature disposed along the lead body proximal to the at least one electrode and configured to assist in atraumatically anchoring the lead to nearby tissue when the lead is positioned in the body. In some variations, the system includes a controllably deformable section including a braided section with controlled buckling points.

The retention features, elements, devices and sections and at least portions of the leads described herein may be modified to promote tissue in-growth. Tissue in-growth may be promoted in a number of ways. The material selected to make or form the retention feature can be one selected because it has micro or macro properties, features or characteristics to promote tissue in-growth. Tissue in-growth can also be promoted by coating a retention element, component, feature, section or portion of the lead with a material having tissue in-growth promoting properties. Exemplary materials that may be used for fabrication and/or coating of the tissue retention features described herein include porous materials with pore sizes of the material selected to provide tissue in growth sites. Other examples of such porous materials include the so-called trabecular metal technology and fiber metal. These materials are used in the orthopedic arts to promote bony in growth into bone implants. A variety of orthopedic implants with such in growth materials are available commercially from orthopedic companies such as Zimmer Inc and are further described at www.zimmer.com. The tissue in-growth material is a modified fiber metal and/or trabecular metal with a growth surface having pores sized to promote tissue in growth rather than bony in-growth. The pore size and other characteristics of the in-growth material will be adjusted depending upon various factors such as the desired implantation site and available tissue types.

The tissue in-growth materials may be used to form or coat the retention features described herein. As a result, the characteristics of the porous material used herein would include modifications to pore size, density and arrangement made to encourage the in growth of soft tissue into the porous structure that forms or coats a retention feature.

The material suited to encourage tissue in growth may be used to form any of the retention features described herein. For example, the porous material could be formed into the shape of a wire with a selected cross section such as round, flat, oval, oblong or any other selected cross section shape. Next, the porous material wire is fabricated into a coiled retention feature as described herein. Alternatively, a porous material may be provided as a coating or a layer bonded, joined, affixed or otherwise attached to a retention feature such as any of the retention features described herein.

It is to be appreciated that the overall dimensions of an individual retention feature, the spacing of one or more retention features along the lead body, the spacing of one or more retention features from another lead component such as, for example, an electrode or the length of the lead body used in the support of one or more retention features will vary depending upon a number of factors and considerations. One consideration for the placement and dimensions of a retention feature is the distance between the targeted neural tissue and the expected retention site. If the distance between the targeted neural tissue and the expected retention site is small, then the spacing between an electrode located at the targeted neural tissue site and a retention feature intended to engage with tissue at the retention site will also be small. In the illustrated embodiment of FIG. 3A, the targeted neural tissue includes the DRG but the retention features 706 are spaced some distance—likely between two and 10 cm—from that location. The spacing may be measured in a direction proximal to or distal to the lead component. The spacing of the retention features 706 in the illustrated embodiment of FIG. 3A is indicated in a proximal direction from the proximal most electrode 704. In contrast, the spacing of the retention features 706 in the illustrated embodiment of FIG. 3B is indicated in a distal direction from the distal most electrode 704. FIGS. 3B, 1B and 2 also illustrate how a distal mounted retention feature remains proximal to the distal end of the lead body. Another consideration is the length or span of the retention feature as it relates to the lead body. This consideration also varies depending upon the specific retention feature design. Consider the individual whiskers 712 in the retention feature 706 of FIGS. 1A and 1B. There are a plurality of individual whiskers 712 that are arrayed along an axial length of the lead body. Similarly, in FIGS. 4-9C, the retention feature 806 are formed into coils 812 that extend along a length of the lead body. While reference has been made to specific embodiments, it is to be appreciated that the all of the retention feature in embodiments described herein may be modified and configured to accommodate the specific physiological circumstances and location with which the retention feature is to secure the lead body relative to the targeted neural tissue. The size, spacing, span, and other physical characteristics of an individual retention feature are selected based on the above considerations.

In one specific example of an embodiment similar to FIG. 4, the spacing between the distal end of the retention feature 806 and the proximal most electrode 804 is about 5 mm or within a range from 5 mm to 10 cm. The length of the retention feature 806 (i.e., the length of the plurality of coils 812) is about 1 cm and can vary within the range of 0.5 cm to 1.5 cm.

In one specific embodiment of the coiled retention features shown and described in FIGS. 4-9C, the coil is formed from a wire. The wire is extruded, flattened or otherwise processed into a generally rectangular cross sectional shape. The degree of rounding of the generally rectangular shape can be adjusted to reduce the likelihood that, when formed into a coiled retention feature, there is little or no damage to the surrounding tissue (i.e., no burrs, rough or sharp edges). Thereafter, the wire is formed into any of the coiled retention features described herein and attached to the lead body as desired. The pitch of the coil winding in any particular embodiment may be adjusted, for example, to enhance the ability of tissue growth in and around the coil, to enhance the ability of the coil to be retained engaged in tissue and other factors determined by the specific coil design and location for implantation. The pitch of the coil or coils in a retention feature may be constant or variable. The pitch of the coil in one location may be selected based on the type of tissue expected to be encountered at that location while another coil on the same lead body may have a different pitch because that coil is intended to engage with the body at another location, potentially different tissue than that engaged by the first retention feature.

In one specific example, a Pt/10%Ir wire of diameter 0.007" is flattened to a rounded rectangular shape with approximate dimensions of 0.003 inch×0.013 inch. The flattened wire is coiled using a conventional coiling process. During the pitch of the coils can be varied during the coiling process for the reasons set forth above. Upon removal from the mandrel, the wrapped wire unwinds to an outer diameter of about 0.037 inch. The coils may be formed into any of a wide variety of lengths depending upon application and the considerations above. Coil lengths may vary from 2 mm to 20 mm depending upon application. Some specific coils of 5 mm length were tested. Exemplary coil pitches include 24 threads per inch (TPI) that results in a thread spacing of 0.042 inch; 34 TPI that results in a thread spacing of 0.030 inch and 58 TPI that results in a thread spacing of 0.017 inch.

In some alternative embodiments, all or a portion of a retaining element, feature or section described herein may include Nitinol components are elements configured such that when the retention element is implanted in the body, the heat produced by the surrounding tissue results in the retention feature deforming into a retention shape.

In other additional embodiments, the functions performed by the stylet 90 or the pusher rod 95 are replaced by a balloon. In these alternative embodiments, the balloon is inflated to provide the necessary stiffening or counter balance force to a normally deformed element. Deflating the balloon or releasing balloon pressure provides a similar result to the removal of a stylet 90 or pusher wire 95. Adjustments in balloon pressure or volume produce similar results to movement of a stylet 90 or pusher wire 95.

It may be appreciated that any of the retention features 706 may optionally be biodegradable or bioabsorbable.

The various alternative retention feature embodiments described herein provide passive retention capability to maintain the position of a lead body within a desired implant location. As such, the various lead retention embodiments described herein provide a lead for stimulating a target neural tissue having an elongate body, at least one electrode disposed along the elongate body; and a passive retention feature disposed along the lead body proximal to the at least one electrode and configured to assist in anchoring the elongate body to tissue near the target neural tissue. In one aspect, the passive retention feature assists in anchoring by friction. In another aspect, at least a portion of the surface of the passive retention feature is treated to increase the friction between the surface of the passive retention feature and surrounding tissue when the lead is implanted in a body. In still other alternatives, the passive retention feature assists in anchoring by tissue ingrowth. In some alternatives, the passive retention feature is disposed along the lead body in a location so as to assist in anchoring to non-neural tissue while the at least one electrode stimulates the target neural tissue. In one aspect, the target neural tissue comprises a dorsal root ganglion. In another aspect, the passive retention feature comprises a coil and, alternatively, the coil is disposed substantially coaxially with the elongate body. In still another variation, the passive retention feature comprises a braided structure configured to buckle in a pre-defined manner. In another alternative, the passive retention feature is fixed in relation to axial movement along the lead body. In still other embodiments, a distal-most end of the passive retention feature is disposed approximately 5 mm to 2 cm proximally of a proximal-most electrode of the at least one electrode.

It may be appreciated that the retention features 706 may optionally be used in combination with suturing techniques. Further, it may be appreciated that the retention features 706 may be used to anchor a variety of different types of leads, including but not limited to cable leads, percutaneous stimulation leads, and paddle-style stimulation leads.

Although the foregoing invention has been described in some detail by way of illustration and example, for purposes of clarity of understanding, it will be obvious that various alternatives, modifications and equivalents may be used and the above description should not be taken as limiting in scope of the invention.

What is claimed is:

1. A system comprising:
 a lead having a lead body and at least one electrode, wherein the lead body is configured for advancement into an epidural space through a needle; and
 a coiled retention feature disposed along the lead body proximal to the at least one electrode,
 wherein the coiled retention feature comprises an unexpandable coil wrapped around a section of the lead body passable through the needle,
 wherein the coiled retention feature is formed from or coated with a material configured to promote tissue in-growth, and
 wherein the coiled retention feature is configured to assist in atraumatically anchoring the lead to nearby tissue within the epidural space by frictional forces when the lead is positioned in the epidural space.

2. The system of claim 1 wherein a diameter of the coiled retention feature is generally constant along a length of the coiled retention feature.

3. The system of claim 1, wherein at least a portion of the coiled retention feature is embedded into the lead body.

4. A lead as in claim 3, wherein the lead body is indented in an area where the coil is embedded into the lead body.

5. A lead as in claim 3, wherein embedding comprises fusing of the coil to the lead body.

6. The system of claim 1, wherein the lead body has a first portion with a first diameter and a second portion with a second diameter that is smaller than the first diameter; and wherein the coiled retention feature is disposed along the second portion.

7. The system of claim 6 wherein a outer diameter of the coiled retention feature is about the same as the first diameter.

8. The system of claim 6 wherein a outer diameter of the coiled retention feature is greater than the first diameter.

9. The system of claim 1 wherein the lead is flexible along the lead body where the coiled retention feature is disposed.

10. The system of claim 1 wherein the coiled retention feature is comprised of a flat wire having a rectangular cross-sectional shape.

11. The system of claim 1 wherein the coiled retention feature is bioresorbable.

12. A system as in claim 1, wherein the nearby tissue is disposed within a back of a patient.

13. A system as in claim 1, wherein the nearby tissue is in the vicinity of a dorsal root ganglion.

14. The system of claim 1 wherein only one end of the coiled retention feature is attached to the lead body.

15. A lead as in claim 1, wherein the coil is comprised of a wire.

16. A lead as in claim 15, wherein the coil has coil turns spaced apart about a distance equal to a width of the wire.

17. A lead as in claim 1, wherein the material is comprised of a porous material having a pore size selected to provide a tissue in-growth site.

18. A lead as in claim 1, wherein the material is comprised of a modified trabecular metal and/or a fiber metal having pores sized to promote tissue in-growth.

19. A lead as in claim 1, wherein the material has a pore size, density or arrangement to encourage in-growth of soft tissue.

* * * * *